(12) United States Patent
Ahn et al.

(10) Patent No.: US 9,289,444 B2
(45) Date of Patent: Mar. 22, 2016

(54) COMPOSITION FOR PROMOTING HEMATOGENESIS CONTAINING QUERCETIN 3-O-β-(2"-GALLOYL)-RHAMNOPYRANOSIDE AS ACTIVE INGREDIENT

(75) Inventors: Byeong Woo Ahn, Cheongju-si (KR); Young Soo Kim, Cheongju-si (KR); Heon Sang Jeong, Cheongju-si (KR); Sang-Kyung Shin, Cheongju-si (KR); Tae-Wang Kim, Seoul (KR); So-Young Youm, Cheongju-si (KR)

(73) Assignee: Chungbuk National University Industry Academic Cooperation Foundation, Cheongju-si (KR)

( * ) Notice: Subject to any disclaimer, the term of this patent is extended or adjusted under 35 U.S.C. 154(b) by 203 days.

(21) Appl. No.: 14/002,850

(22) PCT Filed: Jan. 9, 2012

(86) PCT No.: PCT/KR2012/000213
§ 371 (c)(1),
(2), (4) Date: Sep. 3, 2013

(87) PCT Pub. No.: WO2012/118277
PCT Pub. Date: Sep. 7, 2012

(65) Prior Publication Data
US 2013/0345158 A1 Dec. 26, 2013

(30) Foreign Application Priority Data
Mar. 3, 2011 (KR) .................... 10-2011-0019041

(51) Int. Cl.
*A61K 31/7048* (2006.01)
(52) U.S. Cl.
CPC ......... *A61K 31/7048* (2013.01); *A23V 2002/00* (2013.01)
(58) Field of Classification Search
CPC ................................................. A61K 31/7048
See application file for complete search history.

(56) References Cited

U.S. PATENT DOCUMENTS

2002/0165169 A1* 11/2002 Kim .................. A61K 31/353
514/27

OTHER PUBLICATIONS

Definition of prevent, Oxford English Dictionary Online, http://dictionary.oed.com/, accessed online Mar. 27, 2010, especially definition 9a. at p. 2.*
Alter, B.P., Hematology 2005 ASH Education Book, Jan. 1, 2005, vol. 2005 No. 1, p. 96-103.*
Shin et al., "Quercetin 3-O-β-(2"-galloyl)-rhamnopyranoside promotes the differentiation of hematopoietic stem cells or early progenitor cells into erythroid lineage in mice," *J Medicinal Plants Research* 5(21):5276-5283 (2011).
International Search Report for International Patent Application No. PCT/KR2012/000213, mailed Jul. 31, 2012 (7 pages).

* cited by examiner

*Primary Examiner* — Jonathan S Lau
(74) *Attorney, Agent, or Firm* — Clark & Elbing LLP; Susan M. Michaud

(57) ABSTRACT

This invention relates to a composition for promoting hematopoiesis and for treating, preventing or alleviating cytopenia or bone marrow failure comprising quercetin 3-O-β-(2"-galloyl)-rhamnopyranoside (QGR) as active ingredient. The present active compound QGR (i) increases dose dependently the mRNA expression of cytokines involved in hematopoiesis including stem cell factor, granulocyte-macrophage colony stimulating factor and erythropoietin from mouse bone marrow mononuclear cells, (ii) promotes the formation of burst forming unit-erythroid and colony forming unit-fibroblast, (iii) stimulates the generation of cells positive for TER-119, a specific marker of mouse erythroid precursors, (iv) promotes erythropoiesis, leukopoiesis, thrombopoiesis, and hemoglobin production in bone marrow failure mouse model, (v) stimulates the formation of hematopoietic stem/progenitor cells and mesenchymal stem/progenitor cells, (vi) stimulates megakaryocyte formation surrounding the blood system of damaged bone marrow, osteoid formation and bone marrow restoration through a recovery of damaged bone marrow microenvironment. The QGR of the present invention can be used for promoting hematopoiesis and treating cytopenia or bone marrow failure.

7 Claims, 19 Drawing Sheets

COMPOSITION FOR PROMOTING HEMATOGENESIS CONTAINING QUERCETIN 3-O-β-(2"-GALLOYL)-RHAMNOPYRANOSIDE AS ACTIVE INGREDIENT

CROSS-REFERENCE TO RELATED APPLICATIONS

This application is the U.S. national stage filing under 35 U.S.C. 0371 of PCT International Application No. PCT/KR2012/000213, filed Jan. 9, 2012, which claims priority from Korean Patent Application No. 10-2011-0019041, filed on Mar. 3, 2011, in the Korean Intellectual Property Office, the disclosure of which is incorporated herein by reference.

FIELD OF THE INVENTION

This invention relates to a composition for promoting hematopoiesis and for treating, preventing or alleviating cytopenia (erythropenia, leukopenia, or thrombocytopenia) or bone marrow failure comprising quercetin 3-O-β-(2"-galloyl)-rhamnopyranoside as active ingredient.

DESCRIPTION OF THE RELATED ART

Quercetin 3-O-β-(2"-galloyl)-rhamnopyranoside (QGR) is a polyphenolic compound originally isolated from *Persicaria lapathifolia* S. F. Gray (Polygonacease). *P. lapathifolia* S. F. Gray has traditionally been used for hemostasis. It has been reported that QGR has the effects of inhibiting superoxide production in unopsonized zymosan-stimulated human monocytes, nitric oxide production in lipopolysaccharide (LPS)-stimulated RAW 264.7 macrophage cells and in LPS-induced Balb/c mice. Up to the present, no other pharmacological activity of QGR than an anti-inflammatory effect has been reported.

Hematopoiesis is a process of differentiation of hematopoietic stem cells (HSCs) into the mature blood cells to maintain homeostasis in the body. Hematopoiesis is regulated by several cytokines such as stem cell factor (SCF), IL (interleukin)-3, granulocyte-macrophage colony stimulating factor (GM-CSF), erythropoietin, and thrombopoietin which are secreted from bone marrow stromal cells. Hematopoietic stem cells have to be stably maintained in bone marrow microenvironment for the effective hematopoiesis, more specifically called stem cell niche. Stem cell niche is known as that it includes osteoblastic niche and vascular niche. The number of hematopoietic stem cells is maintained constantly in osteoblastic niche and the stem cells are divided into new cells in response to physiological requirements and then migrate to vascular niche, where the cells are matured and differentiated into eventual blood cells. Thus, the normal function of stem cell niche as well as stem cells is very important in hematopoiesis.

Throughout this specification, various publications and patents are referred and citations are provided in parentheses. The disclosures of these publications and patents in their entities are hereby incorporated by references into this application in order to fully describe this invention and the state of the art to which this invention pertains.

DETAILED DESCRIPTION OF THIS INVENTION

Technical Purposes of this Invention

The present inventors have experimentally demonstrated that a polyphenolic compound quercetin 3-O-β-(2"-galloyl)-rhamnopyranoside isolated from a natural plant has an activity to strengthen the function of hematopoietic stem cell niche inducing the differentiation and proliferation of stem cells into blood cells and as a result promoting hematopoiesis.

Accordingly, it is an object of this invention to provide a composition for promoting hematopoiesis comprising quercetin 3-O-β-(2"-galloyl)-rhamnopyranoside as active ingredient.

It is another object of this invention to provide a composition for treating, preventing or alleviating cytopenia or bone marrow failure comprising quercetin 3-O-β-(2"-galloyl)-rhamnopyranoside as active ingredient.

The present compositions for promoting hematopoiesis and for treating, preventing or alleviating cytopenia or bone marrow failure can be expressed as its use or method.

Other objects and advantages of the present invention will become apparent from the following detailed description together with the appended claims and drawings.

BRIEF DESCRIPTION OF THE DRAWINGS

FIG. 2a represents cell viability treated with various concentrations (μM/ml) of QGR for 24 hrs, FIG. 2b represents cell viability exposed to hypoxic damage for 24 hrs after QGR treatment and FIG. 2c represents cell viability exposed to hypoxic damage for 24 hrs before QGR treatment. Data represented as mean±SD. * Significantly different from negative control ($p<0.01$).

FIG. 9d shows the change of hematocrit (HCT) level which is the percentage of erythrocyte in the blood and becomes low in case of anemia. The pattern of HCT change is similar to that of erythrocytes in FIG. 9a.

DETAILED DESCRIPTION OF THIS INVENTION

Figure 1:
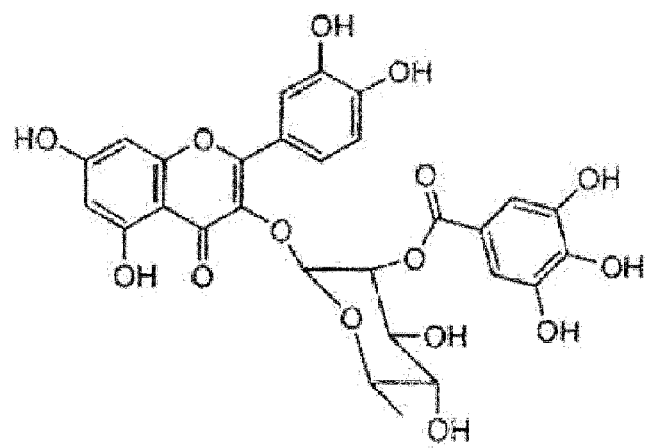
FIG. 1 represents the chemical structure of 3-O-β-(2"-galloyl)-rhamnopyranoside (QGR).

In one aspect of this invention, there is provided a composition for promoting hematopoiesis comprising quercetin 3-O-β-(2"-galloyl)-rhamnopyranoside represented by following formula 1 as active ingredient.

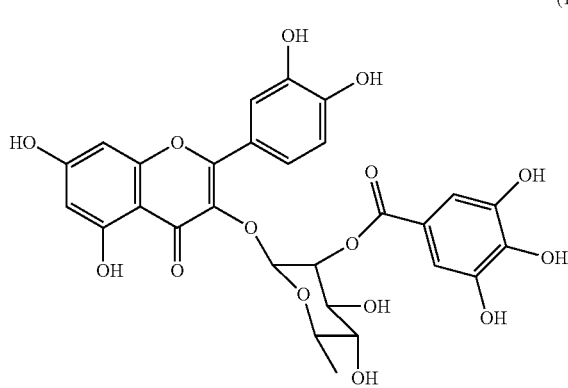

(1)

The present invention is based on the finding the fact that quercetin 3-O-β-(2"-galloyl)-rhamnopyranoside [QGR] can promote hematopoiesis including erythropoiesis, leukopoiesis, or thrombopoiesis and differentiation of bone marrow hematopoietic cells into erythrocyte.

QGR is a polyphenolic compound that can be isolated from *Persicaria lapathifolia* S. F. Gray (Polygonaceae). QGR used as the active ingredient of the present composition can be obtained from the extract of *Persicaria lapathifolia* S. F. Gray or can be chemically synthesized. It is well known to those skilled in the art that chemically synthesized QGR could also have the same effect as much as one obtained from extracts have.

The compound of quercetin 3-O-β-(2"-galloyl)-rhamnopyranoside [QGR] may be prepared according to a conventional method known in the art of purifying and separating a single compound from a natural plant's extract. For example, the compound may be prepared by filtration using silica gel or celite gel column with elution solvent, gel adsorption chromatography, size exclusion chromatography using liquid column chromatography, ion exchange chromatography, partition chromatography, affinity chromatography, or combination thereof but is not limited to.

The present compound of QGR, as demonstrated by the experimental data using a mouse bone marrow mononuclear cells (BMNCs) described in the following specific examples of the present specification, (i) increases dose dependently the mRNA expression of cytokines involved in hematopoiesis including stem cell factor (SCF), granulocyte-macrophage colony stimulating factor (GM-CSF), erythropoietin (Epo), (ii) promotes the formation of burst forming unit-erythroid (BFU-E) which is an early stage cell in the differentiation process from hematopoietic stem cells to erythrocyte, and (iii) stimulates the generation of cells positive for TER-119 a specific marker of mouse erythroid precursors. In addition, as demonstrated from in vivo experiment using a mouse, QGR (i) promotes erythropoiesis, leukopoiesis, thrombopoiesis, and hemoglobin production in bone marrow failure mouse model, (ii) stimulates the formation of HSPCs and MSPCs and the differentiation of CFU-F which is an early stage cell in the differentiation process of mesenchymal stem cell, and (iii) stimulates a megakaryocyte formation surrounding the blood system of damaged bone marrow, an osteoid formation, and a bone marrow restoration through a recovery of damaged bone marrow microenvironment.

In another aspect of this invention, there is provided a composition for treating, preventing or alleviating cytopenia comprising quercetin 3-O-β-(2"-galloyl)-rhamnopyranoside represented by formula 1 as active ingredient.

The term used herein "cytopenia" means a condition in which the level of blood cells such as erythrocytes, leukocytes, and thrombocytes is lower than that of normal or the blood cells are deficient.

The cytopenia includes erythropenia, leukopenia, granulocytopenia, neutropenia, thrombocytopenia, pancytopenia, fanconi's syndrome, myelodysplasia, and anemia but is not limited to.

The cause of cytopenia is very variable, for example, the reduced erythropoietin production due to renal insufficiency, disorder of leukopoiesis in bone marrow such as aplastic anemia, leukemia, cancer in bone marrow, bone marrow stem cells activity degradation due to aging, or bone marrow activity degradation due to side effects of cancer chemotherapy or radiotherapy.

The present compound of QGR stimulates the differentiation of blood cells from bone marrow stem cells and thus can be used to treat, prevent or alleviate cytopenia occurred by various causes.

In still another aspect of this invention, there is provided a composition for treating, preventing or alleviating bone marrow failure comprising quercetin 3-O-β-(2"-galloyl)-rhamnopyranoside represented by formula 1 as active ingredient.

In still another aspect of this invention, there is provided a use of quercetin 3-O-β-(2"-galloyl)-rhamnopyranoside for manufacturing a composition for promoting hematopoiesis.

The composition for promoting hematopoiesis may be a composition for treating, preventing, or alleviating cytopenia.

In still another aspect of this invention, there is provided a method of promoting hematopoiesis comprising administering an effective amount of quercetin 3-O-β-(2"-galloyl)-rhamnopyranoside represented by formula 1 to the subject in need of promoting hematopoiesis.

The subject in need of promoting hematopoiesis may be anyone who is suffering from or at risk of cytopenia. The method of promoting hematopoiesis may be a method of treating, preventing or alleviating cytopenia.

The composition of this invention may be provided as a pharmaceutical composition for treating or preventing cytopenia or bone marrow failure. The pharmaceutical composition of this invention includes a pharmaceutically acceptable carrier besides the active compound.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, acacia gum, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.0001-100 mg/kg (body weight).

The pharmaceutical composition according to the present invention may be administered orally or parenterally, and preferably, administered parenterally, e.g., by intravenous, intraperitoneal, intramuscular, intra-abdominal or transdermal.

According to the conventional techniques known to those skilled in the art, the pharmaceutical composition according to the present invention may be formulated with pharmaceutically acceptable carrier and/or vehicle as described above, finally providing several forms including a unit dose form and a multi-dose form. Non-limiting examples of the formulations include, but not limited to, a solution, a suspension or an emulsion in oil or aqueous medium, an elixir, a powder, a granule, a tablet and a capsule, and may further comprise a dispersion agent or a stabilizer.

The composition of the present invention may be provided as a food composition, particularly a functional food composition. The functional food composition of the present invention may be formulated in a wide variety of forms, for example, including proteins, carbohydrates, fatty acids, nutrients and seasoning agents. In the formulation of drinking agent, it may further include a sweetening agent or natural carbohydrates. For instance, natural carbohydrate may include monosaccharides (e.g., glucose, fructose, etc.); disaccharides (e.g., maltose, sucrose, etc.); oligosaccharides; polysaccharides (e.g., dextrin, cyclodextrin, etc.); and sugar alcohols (e.g., xylitol, sorbitol, erythritol, etc.). The formulation of sweetening agent may use natural sweeteners (e.g., thaumatin, stevia extract, etc.) and synthetic sweeteners (e.g., saccharine, aspartame, etc.). The food composition of the present invention may be much effectively utilized to improve or alleviate cytopenia or bone marrow failure.

The technical features and advantages of the present invention will be summarized as follows:

(i) The active compound quercetin 3-O-β-(2"-galloyl)-rhamnopyranoside [QGR] of this invention promote the differentiation of blood cells from hematopoietic stem cells.

(ii) The active compound QGR of this invention can be used for promoting hematopoiesis.

(iii) The active compound QGR of this invention can be used for promoting erythropoiesis, leukopoiesis, thrombopoiesis, and hemoglobin production.

(iv) The active compound QGR of this invention can be used for treating, preventing or relieving cytopenia.

(v) The active compound QGR of this invention can be used for treating or alleviating damaged or malfunctioned bone marrow.

Advantageous Effects

This invention relates to a composition for promoting hematopoiesis and for treating, preventing or alleviating cytopenia or bone marrow failure comprising quercetin 3-O-β-(2"-galloyl)-rhamnopyranoside as active ingredient. The present active compound QGR (i) increases dose dependently the mRNA expression of cytokines involved in hematopoiesis including stem cell factor, granulocyte-macrophage colony stimulating factor, erythropoietin from mouse bone marrow mononuclear cells, (ii) promotes the formation of burst forming unit-erythroid and colony forming unit-fibroblast, (iii) stimulates the generation of cells positive for TER-119, a specific marker of mouse erythroid precursors, (iv) promotes erythropoiesis, leukopoiesis, thrombopoiesis, and hemoglobin production in bone marrow failure mouse model, (v) stimulates the formation of hematopoietic stem/progenitor cells and mesenchymal stem/progenitor cells, (vi) stimulates megakaryocyte formation surrounding the blood system of damaged bone marrow, osteoid formation and bone marrow restoration through a recovery of damaged bone marrow microenvironment. The QGR of the present invention can be used for promoting hematopoiesis and treating cytopenia or bone marrow failure.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods

1. Experiments for Effect of QGR on Mouse Bone Marrow Mononuclear Cells (1) Reagents Mouse recombinant IL-3 (rIL-3), recombinant SCF (rSCF) and recombinant Epo (rEpo) proteins, biotinylated rat monoclonal anti-mouse TER-119 and phycoerythrin (PE)-conjugated monoclonal anti-TER-119 were purchased from R&D Systems (Minneapolis, Minn., USA). Quercetin 3-O-β-(2"-galloyl)-rhamnopyranoside (QGR, >98% pure) was isolated from aerial part of *P. lapathifolia* as described previously (Kim et al., Flavonol glycoside gallate and ferulate esters from *Persicaria lapathifolia* as inhibitors of superoxide production in human monocytes stimulated by unopsonized zymosan. Planta Med 66, 72-74, 2000). QGR was dissolved in dimethylsulfoxide to a final concentration of 100 mM as the stock solution and was diluted in culture medium before treatment.

(2) Isolation of Bone Marrow Mononuclear Cells and Stromal Cells

Bone marrow mononuclear cells (BMNCs) were isolated from femurs and tibias of 8 to 12-week-old male C57BL/6 mice by a previously described protocol [Kroeger K, Collins M, Ugozzoli (2009) The preparation of primary hematopoietic cell cultures from murine bone marrow for electroporation. J. Vis. Exp. 23: pii:1026. doi:10.3791/1026] and were separated from dead cells and red blood cells (RBCs) by Histopaque (1,077 g/ml) (Sigma-Aldrich Chemical, St. Louis, Mo., USA) density gradient centrifugation. Thereafter, the cells were cultured in Iscove's modified Dulbecco's media (IMDM) with 15% heat inactivated fetal bovine serum (FBS), 1% bovine serum albumin (BSA), 100 units/ml penicillin and 100 µg/ml streptomycin at 37° C. in 5% $CO_2$ humidified air. The separated blood was cultured as described previously [Oswald J, et al. (2004). Mesenchymal stem cells can be differentiated into endothelial cells in vitro. Stem Cells, 22: 377-384.] to obtain bone marrow stromal cells in α-minimum essential medium (MEM) with 20% heat inactivated FBS, 100 units/ml penicillin and 100 µg/ml streptomycin at 37° C. in 5% $CO_2$ humidified air.

(3) Cell Viability Assay

The possible cytotoxicity of QGR was examined in BMNCs. The cells were plated with a density of $5 \times 10^3$ cells/well in 96 well plates in 200 µl of medium. The cells cultured for 24 hrs with variable concentrations of QGR in either normoxia or hypoxia conditions were evaluated using a cell counting-8 assay kit (CCK-8) according to the manufacturer's instructions (Dojindo Molecular Technologies, Rockville, Md., USA). Briefly, 20 µl of CCK-8 solution was added to each well. The plates were incubated for 2 hrs in an incubator at 37° C. The resulting color was assayed at 450 nm using an EL808 microplate absorbance reader (BIO-TEK, Winooski, Vt., USA).

(4) Real-Time Reverse Transcription-Polymerase Chain Reaction

To confirm whether QGR regulates the expression of hematopoietic cytokines in bone marrow stromal cells, real-time RT-PCR was performed. Bone marrow stromal cells ($3 \times 10^5$ cells/plate) were incubated with either mouse rIL-3 (100 units/ml) plus rSCF (5 units/ml) plus rEpo (3 units/ml) or QGR (50, 100 or 200 µM/ml) in 60 mm-diameter cell culture plates. The cells were harvested after 4 hr of incubation and washed with PBS and total RNA were extracted using RNA extraction kit (Applied Biosystems, Carlsbad, Calif., USA). First strand synthesis of cDNA was carried out with 1 µg of total RNA using cDNA synthesis kit (Applied Biosystems, Foster City, Calif., USA). Real-time PCR using TaqMan probe PCR master mix kit (Applied Biosystems) was performed according to the manufacturer's instruction using a model 7500 Real-Time PCR System (Applied Biosystems).

The sequences of primers used are indicated in Table 1. GAPDH mRNA was utilized as an internal standard to normalize target transcript expression. The relative ratios of SCF, GM-CSF, or Epo mRNA to GAPDH mRNA which can be used to quantify precisely the levels of each mRNA expression, were calculated with the standard curves.

TABLE 1

| The primers used in real-time RT-PCR | | |
|---|---|---|
| Genes | Sequence | NCBI ref.seq. |
| GAPDH | 5'-TGCATCCTGCACCACCAACTGCTTAG-3' (FAM) | NM_008084.2 |
| SCF | 5'-CATTACAAAACTGGTGGCAAATCTT-3' (FAM) | NM_013598.2 |
| GM-CSF | 5'-GCCCCCCAACTCCGGAAACGGACTG-3' (FAM) | NM_009969.4 |
| Epo | 5'-AGAAAATGTCACGATGGGTTGTGCA-3' (FAM) | NM_007942.2 |

(5) Semisolid Colonogenic Assay

To investigate the effects of QGR on erythroid lineage development in mouse HSCs and EPCs, the colonogenic assay was performed according to the manufacturer's instruction in triplicate by plating $2 \times 10^5$ cells/plate using methylcellulose stock solution in IMDM (R&D Systems) with cocktail (rIL-3 100 units/ml plus rSCF 5 units/ml plus rEpo 3 units/ml) or/and QGR (0, 100 or 200 µM/ml) in 35 mm-diameter cell culture plates. These plates were put in 100 mm-diameter plates with 3 ml of autoclaved distilled water and incubated at 37° C. in 5% $CO_2$ humidity air. 14 days later, BFU-E colonies were counted under an Axiovert 40 CFL inverted microscope (Carl Zeiss, Oberkochen, Germany).

(6) Histochemistry and Immunocytochemistry for Erythroid Cells

In order to investigate whether QGR can stimulate the differentiation of hematopoietic stem cells into erythroid cells, the morphology of cells was observed and immunocytochemistry against TER-119, the marker of erythroid progenitors, was carried out. BMNCs were harvested 7 days after incubation with either rEpo (3 units/ml) or QGR (100 or 200 µM/ml) washed with PBS, re-suspended at a concentration of $2 \times 10^5$ cells/ml in PBS and subjected (100 µl/slide) to cytospin for 5 min at 1,000 rpm (Cytospin3; Shandon, ThermoElectron, Waltham, Mass., USA). All slides were fixed using cold methanol. Wright-Giemsa stain was performed for morphologic analysis. Immunocytochemistry against TER-119 was carried out for cellular lineage with 100-fold dilution according to the manufacturer's instruction using avidin biotinylated enzyme complex kit (VECTASTAIN, Vector Laboratories and Burlingame, Calif., USA).

(7) Flow Cytometric Analysis for Cells Positive for TER-119

To confirm the differentiation of mouse HSCs or EPCs into erythroid cells by QGR treatment, flow cytometric analysis for mouse anti-TER-119 was performed. BMNCs were cultured with either rEpo (3 units/ml) or QGR (100 or 200 µM/ml) in 6-well plates. Cells were harvested at day 7, washed with PBS, re-suspended at concentration of $1 \times 10^5$ cells/ml in 100 µl of PBS containing 0.02% sodium azide and 2% FBS, incubated with 10 μl of mouse anti-CD16/CD32 Ab (eBioScience, San Diego, Calif., USA) as $F_c$ receptor blocker for 3 min at room temperature and incubated with PE-conjugated anti-TER-119 Ab for 20 min at 4° C. Flow cytometric analysis was performed using FACS Calibur (Becton Dickinson, Oxnard, Calif., USA) and the percentage of positively stained cells was determined.

(8) Statistical Analysis

Data are represented as mean±S.D. of three independent replicates. Statistical comparisons were made using the Student-Newman-Keuls (SNK) t-test after one-way ANOVA using SAS 9.1 program.

2. Experiments for the Effect of QGR on a Bone Marrow Failure Mouse Induced by Administration of Busulphan (BU)

(1) Animals 5-week-old female Balb/c mice were purchased from Orient Bio Inc. (Seongnam-si, Gyeonggi-do, Korea). All protocols of animal experiments were approved by Institutional Animal Care and Use Committee of Laboratory Animal Research Center, Chungbuk National University. The mice were fed by Teklad Global 18% protein rodent diet (Harlan, Iowa, USA) and had free access to drinking water. The mice were housed and bred under specific pathogen-free conditions, and were went through environmental acclimatization for one week before used in the animal experiments and were separated into three groups (n=70/group).

(2) Experiment Design

Figure 8:
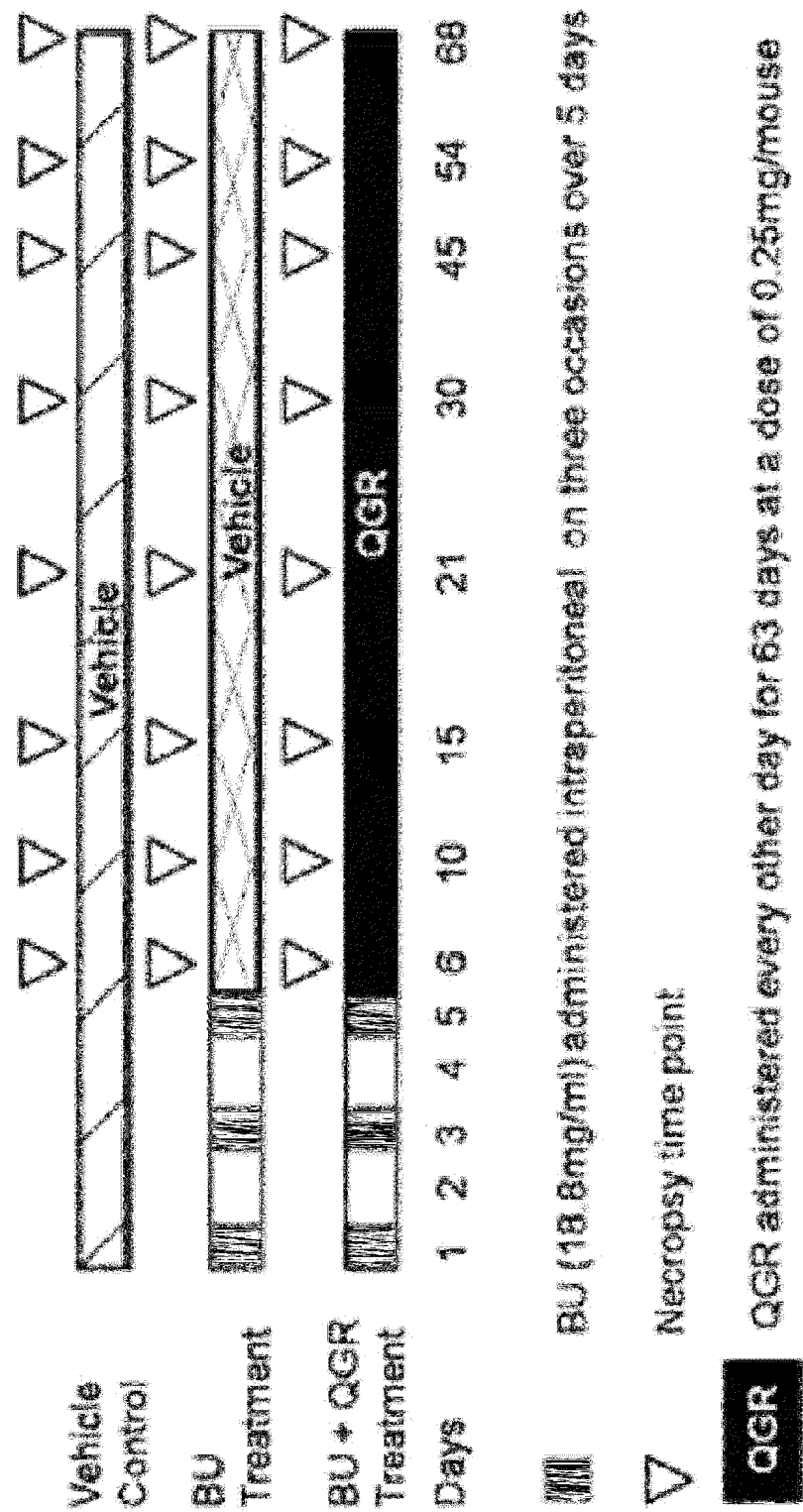
FIG. 8 shows the experimental design using mice.

Bone marrow failure model induced by administering busulphan (BU) was designed according to the procedures previously described by Molyneux et al (Cell Biol Toxicol 27, 13-40, 2011) and the scheme is shown in FIG. 8. BU (Sigma chemicals, Poole, Dorset, UK) was dissolved in acetone to a final concentration of 18.8 mg/ml, diluted five-fold with distilled water, and was intraperitoneally administered three times for 5 days with the dose of 0.2 ml BU solution per mouse. Equal amount of five-fold diluted acetone solution without BU was administered to vehicle control group. QGR was dissolved in dimethylsulfoxide and diluted with distilled water to a final concentration of 1.25%. Mice were orally administered every two days with QGR (0.25 mg/mouse) for 63 days. Seven or eight mice were sacrificed on days of 1, 5, 10, 16, 25, 40, 49, and 63 after BU administration and were investigated to confirm the effect of QGR to recover bone marrow failure.

(3) Peripheral Blood Analysis

In order to evaluate the activity of QGR to recover anemia animal model induced by BU administration, peripheral blood was collected during an autopsy and were investigated. The collected peripheral blood was stored in the bottle containing EDTA to prevent a blood clotting, and the numbers of erythrocytes, leukocytes, and platelets, hematocrit (HCT) level, mean corpuscular volume (MCV), and mean corpuscular hemoglobin (MCH) were measured.

(4) Flow Cytometric Analysis

In order to investigate whether QGR has an activity to recover bone marrow failure induced by BU administration, the expression of markers associated with hematopoietic stem cells/progenitors (Sca-1$^+$ or c-kit$^+$), bone mesenchymal stem/progenitor cells (Sca-1$^+$CD44$^+$), apoptotic hematopoietic stem cells (c-Kit$^+$7-aminoactinomycin D$^+$) were measured by flow cytometry. The retrieved BMNCs with the concentration of $0.6 \times 10^6$ cells/ml were precipitated by centrifugation, re-suspended in 100 μl of PBS containing 0.02% sodium azide and 2% FBS, and incubated with 10 μl of mouse anti-CD16/CD32 Ab (eBioScience, San Diego, Calif., USA) as FC receptor blocker for 3 min at room temperature. After that, monoclonal antibodies for c-kit (2B8, BD Pharmingen, USA), Sca-1 (D7, eBioscience), CD44 (IM7, eBioscience) were added and further incubated for 30 min under the temperature of 4° C. Isotype-matched irrelevant rat $IgG_{2b}$-FITC (eBioscience) and isotype-matched irrelevant rat $IgG_{2a}$-PE (eBioscience) were used as negative control. The flow cytometric analysis was carried out using FACS Calibur (Becton Dickinson, Oxnard, Calif., USA) and the percentage of positively stained cells was determined. The double staining of c-kit and 7-AAD (Calbiochem-Novabiochem, Nottingham, UK) was carried out according to the procedures previously described by Philpott et al (Exp Hematol, 23, 1642-1648, 1995).

(5) Semisolid Colonogenic Assay for Measuring BFU-E

In order to investigate whether QGR has an activity to promote the differentiation from hematopoietic stem cells to BFU-E namely an erythroid progenitor in the damaged bone marrow induced by BU administration, the semisolid colonogenic assay was carried out. BMNCs were plated in $2 \times 10^5$ cells/plate using methylcellulose stock solution in IMDM (R&D Systems) with cocktail (rIL-3 100 units/ml plus rSCF 5 units/ml plus rEpo 3 units/ml) or/and QGR (0, 100 or 200 μM/ml) in 35 mm-diameter cell culture plates. 14 days later, the number of BFU-E colony was counted.

(6) Isolation of Mesenchymal Stem/Progenitor Cells (MSPCs) and Measurement of Colony-Forming Unit-Fibroblast (CFU-F)

CFU-F, a progenitor cell colony differentiated from MSPCs is in the stage prior to being finally matured into mesenchymal cells such as osteoblast, vascular endothelial cells acting as hematopoietic stem cell niche. In order to investigate the effect of QGR on the formation and differentiation of mesenchymal stem cells, MSPCs were isolated and the number of CFU-F colonies of the respective groups was measured and compared to each other. The isolation of MSPCs was performed according to the procedures previously described by Nadri et al (An efficient method for isolation of murine bone marrow mesenchymal stem cells. Int J Dev Biol, 51, 723-729, 2007). To compare the colony formation potential, 100 cells were plated in a 60 mm$^2$ cell culture dish and incubated for 7 days. Subsequently, the plates were stained with 3% crystal violet in methanol for 10 min. All visible colonies were counted.

(7) Histopathological Features of Bone Marrow and Measurement of Osteoid Formation In order to confirm histological bone marrow damage induced by BU administration and to investigate whether QGR recovers the damaged bone marrow, histopathological features of H&E staining slide of the respective group's bone marrow were observed and compared to each other among the groups. In addition, the degree of sinusoid damage in bone marrow was graded as normal, hemorrhage or discontinuous, regressed vessel, assigned with numerical value and compared to each other among the groups. Moreover, in order to investigate the effect of QGR on the differentiation and maturation from mesenchymal stem cells to osteoblast, the formation of osteoid in humerus was comparatively analyzed. Goldner's trichrome staining was carried for osteoid and the stained area of the respective group was compared with each other after determining the stained area by using an image analyzer.

(8) Statistical Analysis

Data are represented as mean±S.D. of three independent replicates. Statistical comparisons were made using Tukey t-test and Fisher's exact test after one-way ANOVA using SAS 9.1 program.

Results

Figure 2A:
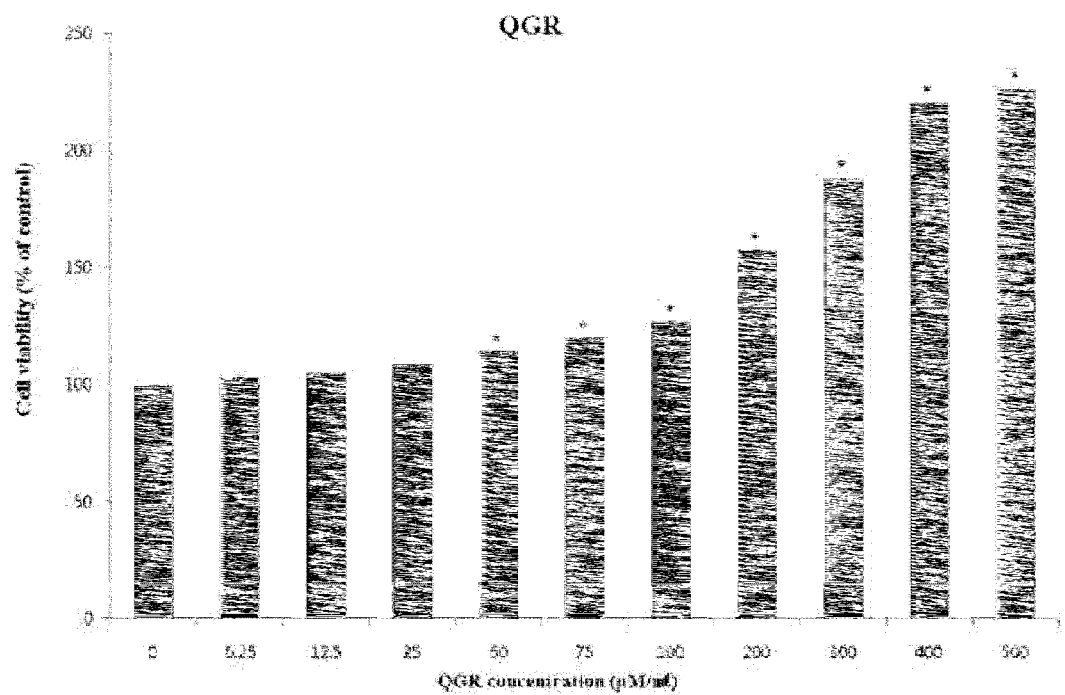
FIGS. 2a-2c show the effect of QGR on cell viability.
Figure 2B:
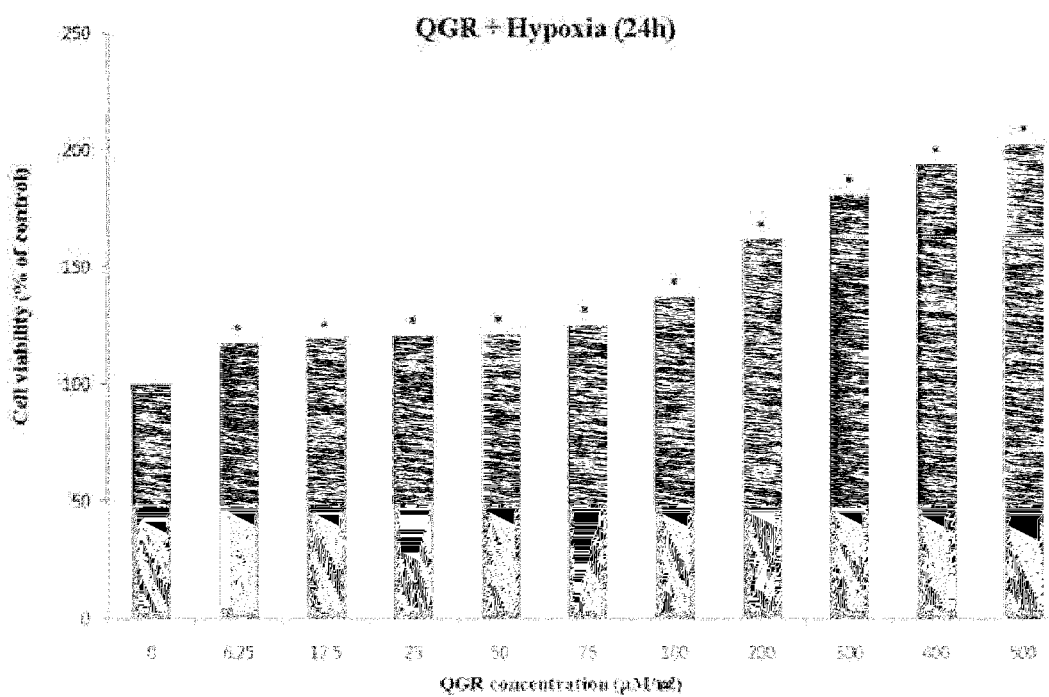
Figure 2C:
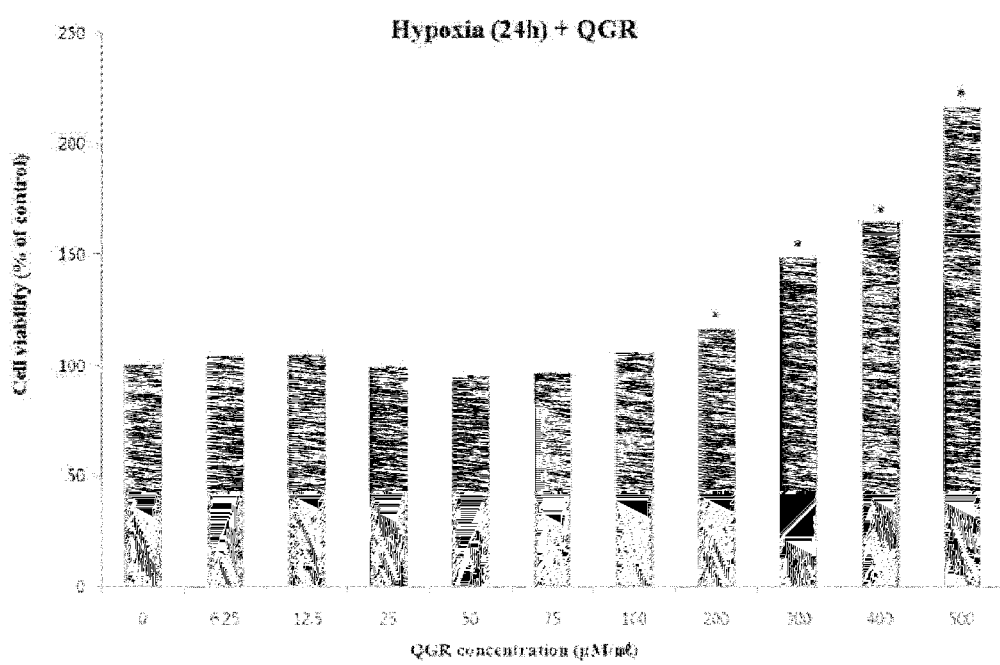

1. Results of Experiments on Bone Marrow Mononuclear Cells (1) The Effect of QGR on Cell Viability QGR was not cytotoxic and significantly increased cell viability at the concentration of 50 μM (FIGS. 2a, 2b, and 2c). Pretreatment of QGR increased the viable cells under hypoxic damage in a dose-dependent manner compared to the untreated group. QGR post-treatment at the concentrations of 200 μM increased cell viability after hypoxic damage for 24 hrs.

(2) The Effect of QGR in the Expression of Hematopoiesis-Related Cytokines

Figure 3:
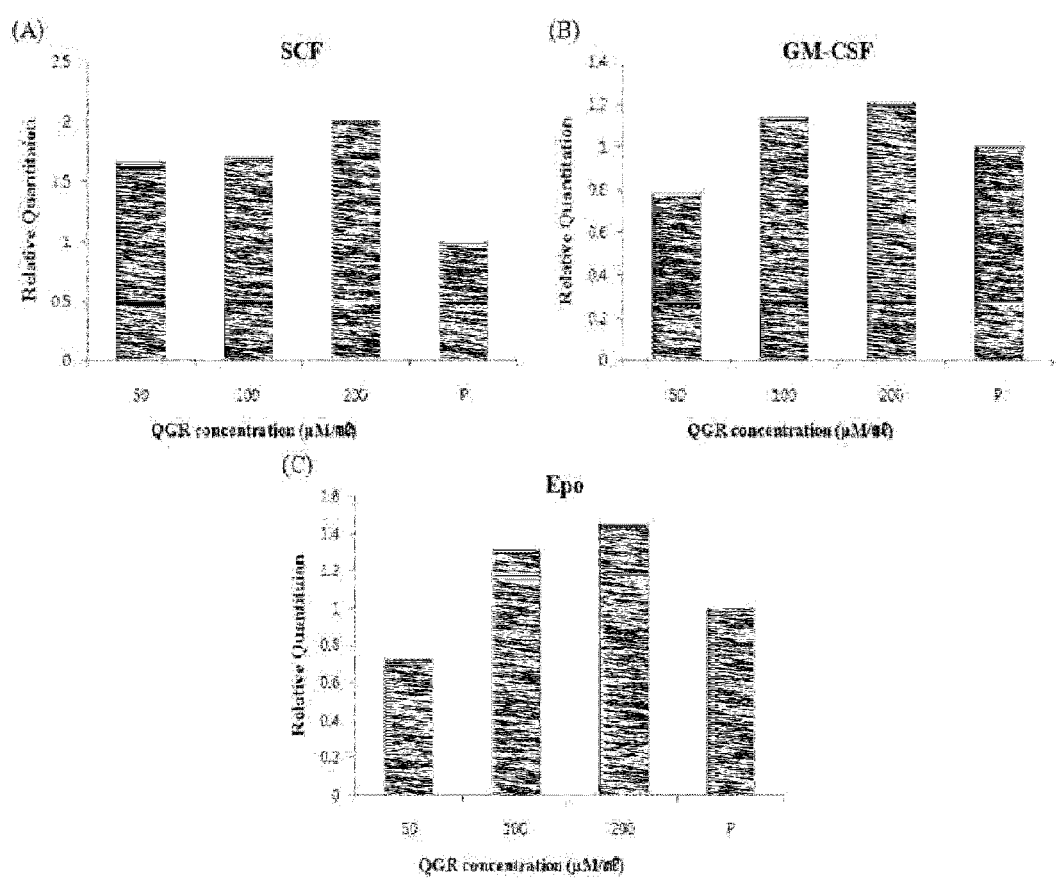
FIG. 3 shows the effect of QGR on mRNA expression of hematopoietic cytokines in the bone marrow stromal cells. The cells were treated with either rIL-3+rSCF+rEpo as positive control (P), or QGR (50, 100 or 200 μM/ml) as treatment group for 4 hrs. The mRNA expressions of SCF (A), GM-CSF (B) and Epo (C) were measured by real-time RT-PCR. The levels are indicated as a relative ratio against positive control.

QGR increased the mRNA expression levels of SCF, GM-CSF and Epo from bone marrow stromal cells in a dose-dependent manner (FIG. 3). QGR significantly increased the SCF at all concentrations when compared to the positive control. The GM-CSF and Epo were significantly increased at the concentrations of 100 and 200 μM QGR when compared to the positive control.

(3) The Effect of QGR on the Formation of BFU-E Colony

Figure 4:
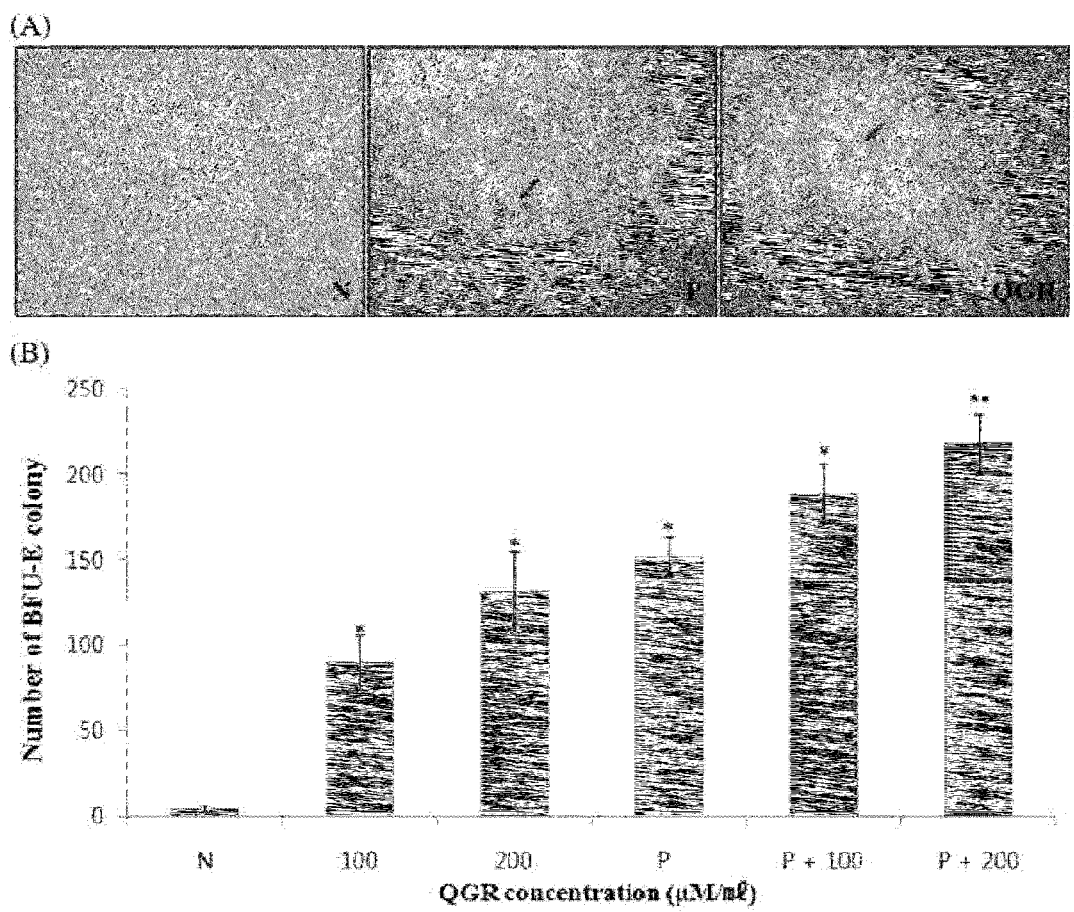
FIG. 4 shows the effect of QGR on the formation and growth of BFU-E (burst forming unit-erythroid) colony. The bone marrow mononuclear cells (BMNCs) were treated with either rIL-3+rSCF+rEpo as positive control (P), or QGR (100 or 200 μM/ml) as treatment group. The morphology of BFU-E (A) was assessed by the hematopoietic progenitor cell colony-forming assay on day 14. BFU-E colonies indicated by arrow significantly increased in positive control (P) and treatment group (QGR), and were hardly observed in negative control (N). The numbers of BFU-E colonies were counted and data are represented as mean±SD of three independent replicates. * Significantly different from negative control ($p<0.001$) and ** significantly different from negative and positive control.

As shown in FIG. 4, the treatment of QGR to BMNCs significantly enhanced the number of BFU-E (burst forming unit-erythroid) colonies in a dose-dependent manner compared with negative control ($p<0.001$). Specifically, according to the panel (B) of FIG. 4, the number of BFU-E colony induced by the treatment of QGR is significantly larger than that of negative control although it is smaller than that of positive control. In addition, the treatment with the cocktail (rIL-3, rSCF and rEpo) plus 200 μM QGR significantly increased the formation and growth of BFU-E colonies 1.43-fold compared with the positive control ($p<0.01$).

(4) The Effect of QGR on the Stimulation of Erythroid Differentiation

Figure 5:
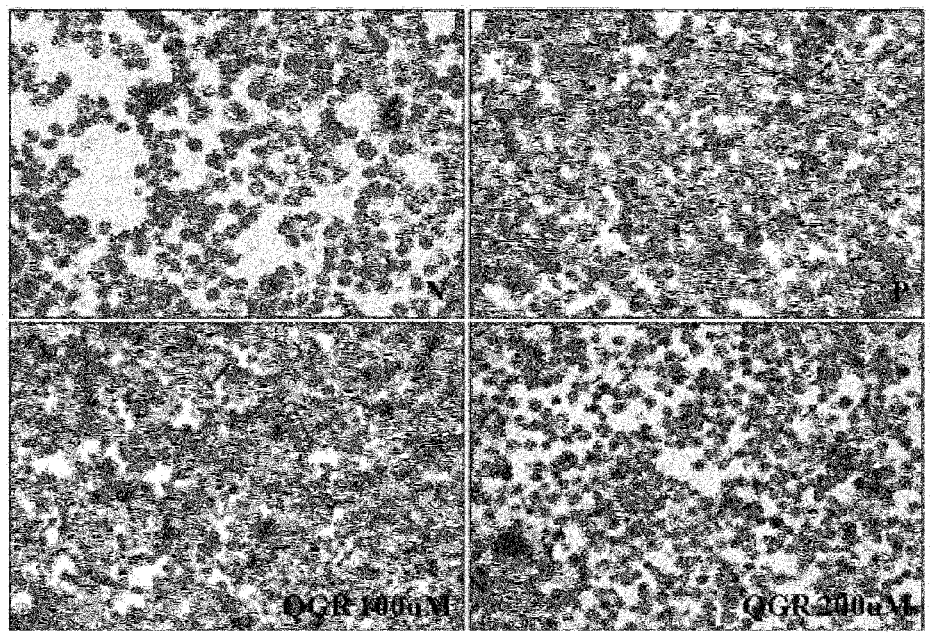
FIG. 5 shows the result of morphological analysis of BMNCs cultured for 7 days after treatment with rEpo as a positive control group (P) or QGR as an experimental group (100 or 200 μM/ml). The number of enucleated erythroid cells indicated as an arrow increased in the QGR treatment group (Wright-Giemsa staining, ×400).
Figure 6:
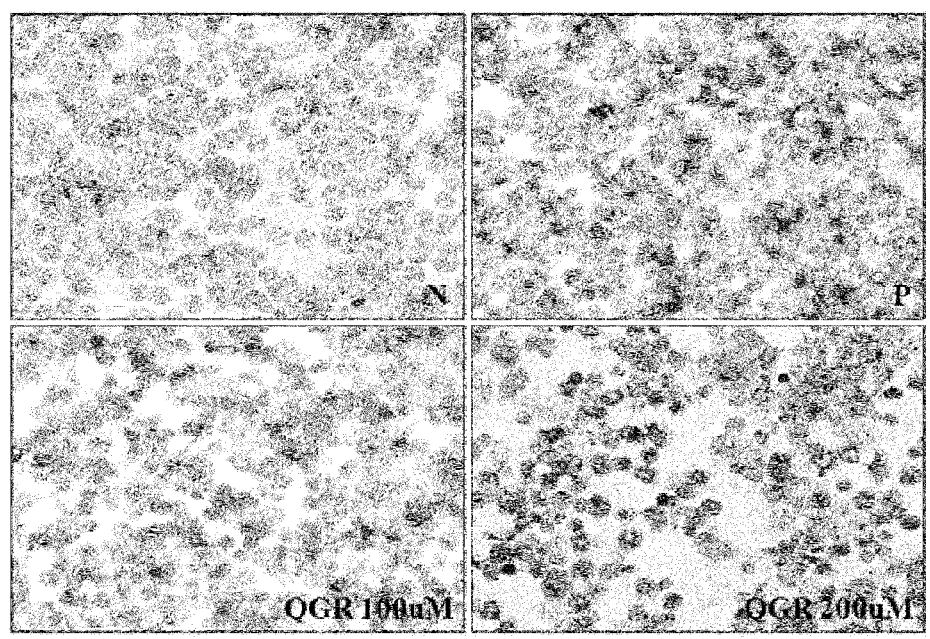
FIG. 6 shows the result of immunocytochemical analysis for erythroid surface antigen of BMNCs cultured for 7 days after treatment with rEpo as a positive control group (P) or QGR as an experimental group (100 or 200 μM/ml). The number of TER-119 positive cells in the QGR treatment group increased (ABC, ×400).
Figure 7A:
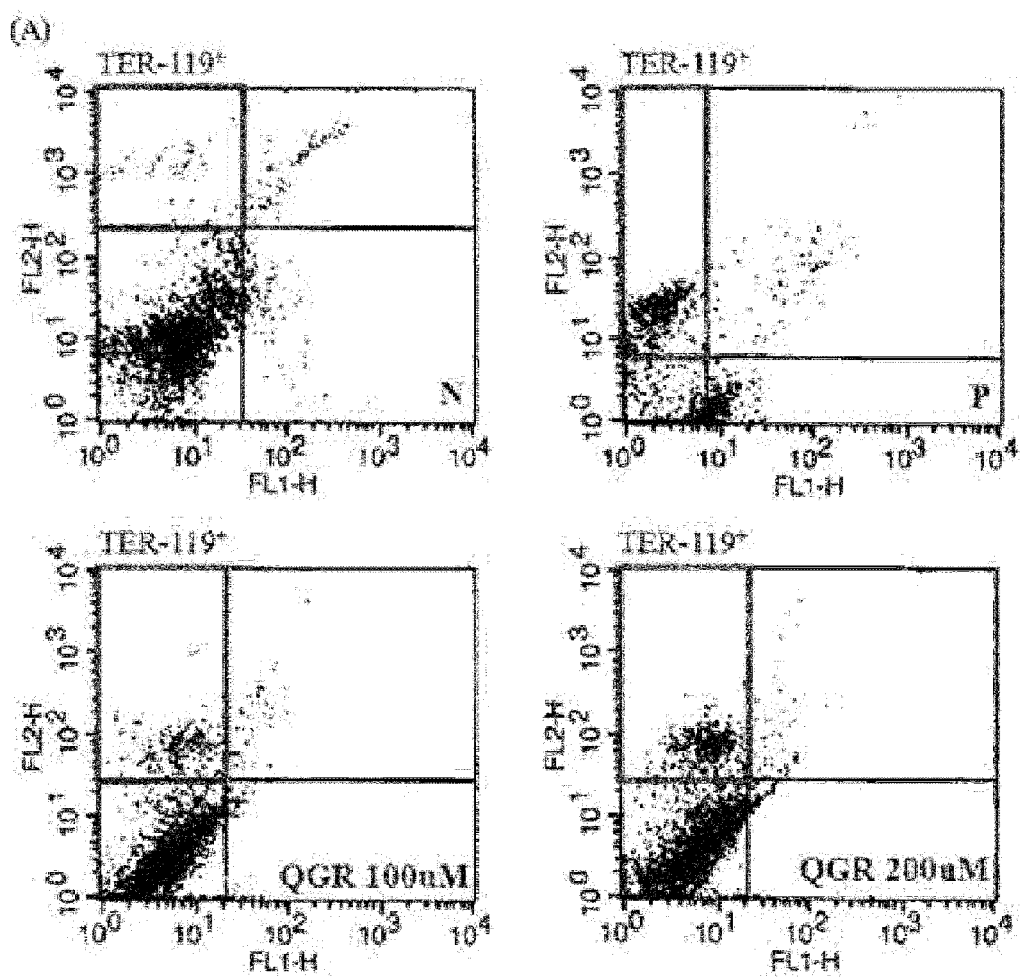
FIGS. 7a and 7b show the effect of QGR on the differentiation of BMNCs determined by a flow cytometric analysis. The cells cultured for 7 days after treatment with rEpo (positive control group) and QGR (100 or 200 μM/ml, experimental group) were stained with antibody against TER-119. Gate was set for cells positively stained with PE-conjugated antibody against TER-119 (FIG. 7a). The number of cells positive for TER-119 in the respective group is expressed as a relative ratio against that of negative control group (FIG. 7b). Data represented as mean±SD of three independent replicates. * significantly different from negative control (p<0.01).
Figure 7B:
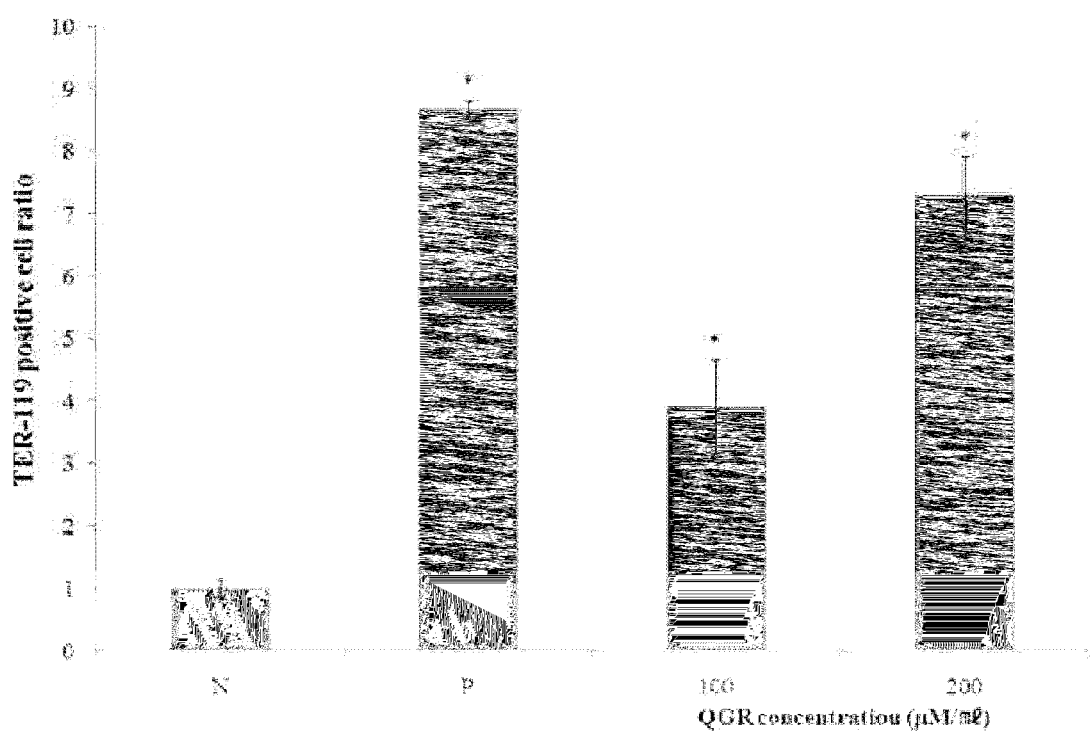

As shown in FIG. 5, the number of enucleated erythroid cells increased in the positive control group and QGR treatment group. Immunocytochemical analysis for the TER-119, an erythroid surface antigen showed that TER-119$^+$ cells increased in the QGR-treated group compared to the negative control (FIG. 6). In flow cytometric analysis for TER-119, the ratio of TER-119$^+$ cells was significantly increased in the QGR treatment group dose-dependently when compared to the negative control (FIGS. 7a and 7b).

Figure 9A:
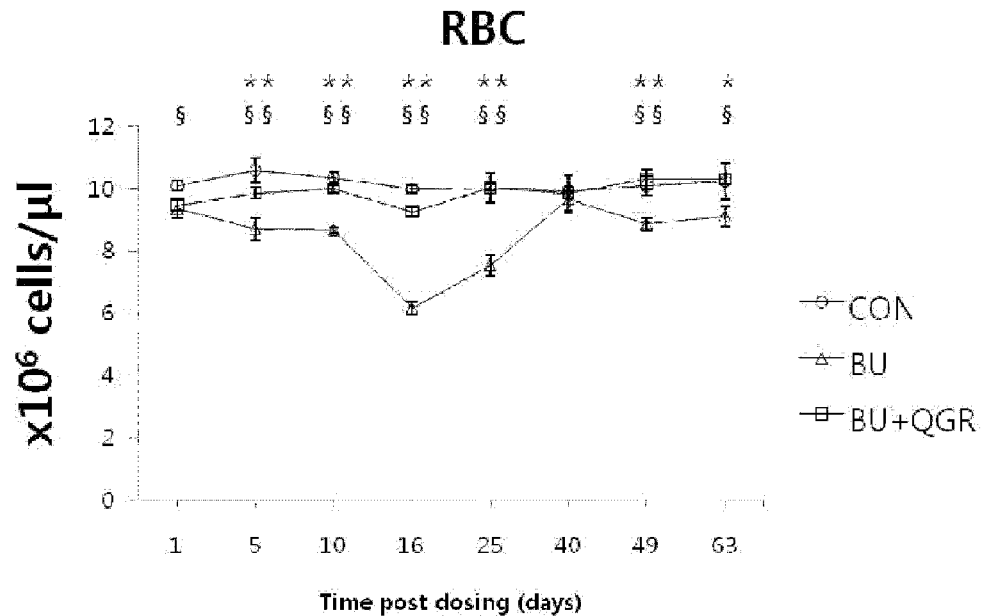
FIG. 9a shows the change of the erythrocyte (red blood cells) level. The erythrocyte level in busulphan (BU) administration group (positive control group, vehicle administration after BU administration) decreased continuously after BU administration, reached the lowest level at day 16, and after that, recovered gradually and arrived at the normal level at day 40. The positive control group suffered from chronic anemia after day 40 (§§: p<0.01, §: p<0.05). The erythrocyte level of BU+QGR administration group (experimental group, QGR administration after BU administration) was slightly lower than that of normal control group, but it was significantly higher than that of positive control group. At days 5, 10, 16, 25, 49, and 63 after QGR administration, the erythrocyte level was significantly higher than that of positive control group (**: p<0.01, *:p<0.05).

2. Results from the Experiment for Effect of QGR on a Mouse Bone Marrow Failure Model (1) Peripheral Blood Analysis FIG. 9a shows the change of erythrocyte numbers. The numbers of erythrocyte in BU administration group (positive control group, vehicle administration after BU administration) decreased continuously after BU administration, reached the lowest level at day 16, and after that, recovered gradually and arrived at the normal level at day 40. The positive control group suffered from chronic anaemia after day 40 (§§: $p<0.01$, §: $p<0.05$). The erythrocyte level in BU administration group was precisely consistent with the results provided by Molyneux et al (Cell Biol Toxicol, 27, 13-40, 2011) who had made this animal model. The erythrocyte level of BU+QGR administration group (experimental group, QGR administration after BU administration) was slightly lower than that of normal control group, but it was significantly higher than that of positive control group. At days 5, 10, 16, 25, 49, and 63 after QGR administration, the levels of erythrocytes were significantly higher than those of positive control group (**: $p<0.01$, *: $p<0.05$). In summary, QGR showed a recovery effect on erythrocyte level from day 5.

Figure 9B:
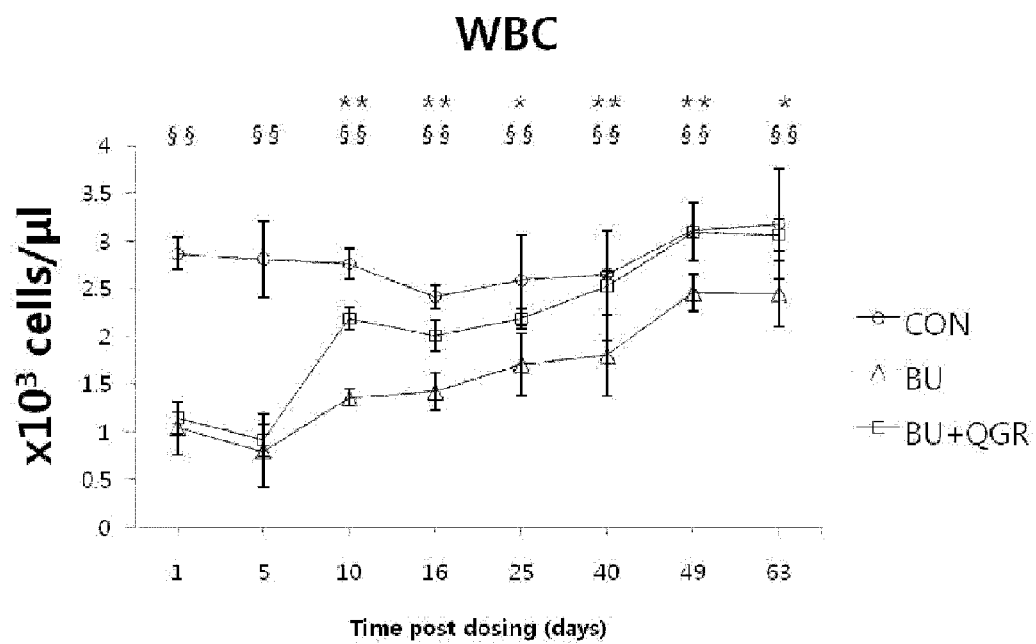
FIG. 9b shows the change of the leukocytes (white blood cells) level. The leukocytes number in BU administration group (positive control group, vehicle administration after BU administration) was significantly decreased from day 1 to day 63 (§§: p<0.01, §: p<0.05). On the contrary, the leukocytes level of BU+QGR administration group (experimental group, QGR administration after BU administration) was slightly lower than that of normal control group, but started to increase at day 10 and continuously increased up to day 63 maintaining higher level than that of positive control group (**: p<0.01, *: p<0.05).

FIG. 9b shows the change of the leukocyte (white blood cells) numbers. The leukocyte numbers of BU administration group (positive control group, vehicle administration after BU administration) were significantly lower from day 1 to day 63 (§§: $p<0.01$, §: $p<0.05$). On the contrary, the those of BU+QGR administration group (experimental group, QGR administration after BU administration) were slightly lower than that of normal control group, but started to increase at day 10 and continuously increased up to day 63 maintaining higher level than those of positive control group (**: $p<0.01$, *: $p<0.05$). In summary, QGR showed a recovery effect of leukocyte level from the day 10.

Figure 9C:
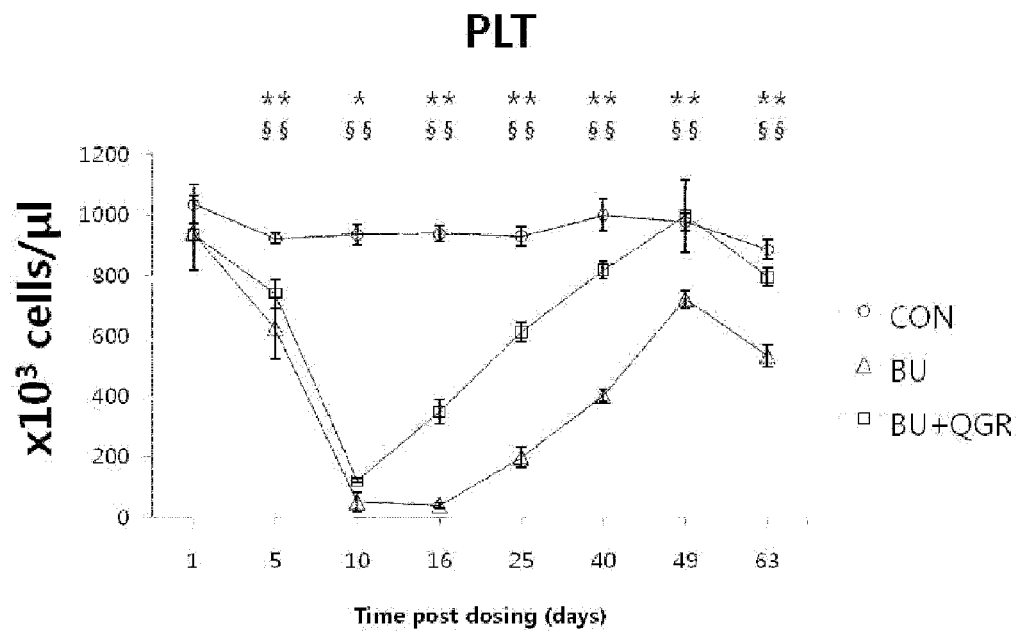
FIG. 9c shows the change of the platelet level. In the positive control group (vehicle administration after BU administration), the number of platelets dramatically decreased up to day 10 by BU administration and after that recovered gradually to maximal level at day 49, and finally the positive control group suffered from chronic thrombocytopenia after day 49. On the contrary, when QGR was administered (BU+QGR), the platelet numbers steeply recovered and had a significant difference continuously from the positive control group (**: p<0.01, *: p<0.05).

FIG. 9c shows the change of the platelet numbers. In the positive control group, the number of platelets dramatically decreased up to day 10 by BU administration and after that, recovered gradually to maximal level at day 49. The positive control group suffered from chronic thrombocytopenia after day 49. On the contrary, when QGR was administered, the platelet numbers steeply recovered and showed significant differences continuously from the positive control group (**: $p<0.01$, *: $p<0.05$). In summary, from day 16, QGR recovered the reduced platelet numbers.

Figure 9D:
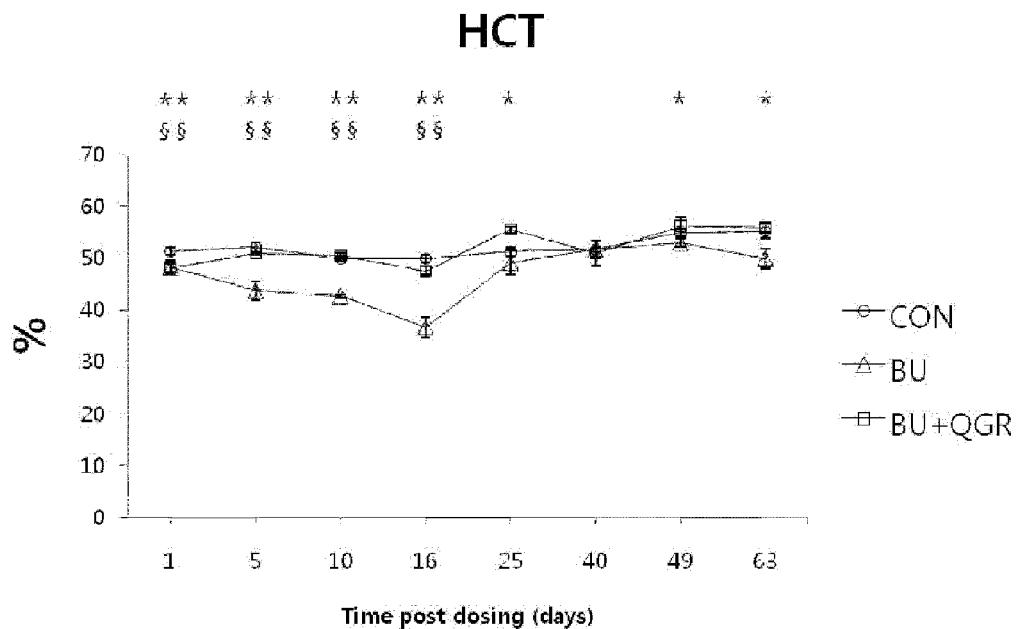

FIG. 9d shows the change of hematocrit (HCT) level which is the percentage of erythrocyte in the blood and becomes low in case of anemia. The pattern of HCT change is similar to that of erythrocytes in FIG. 9a.

Figure 9E:
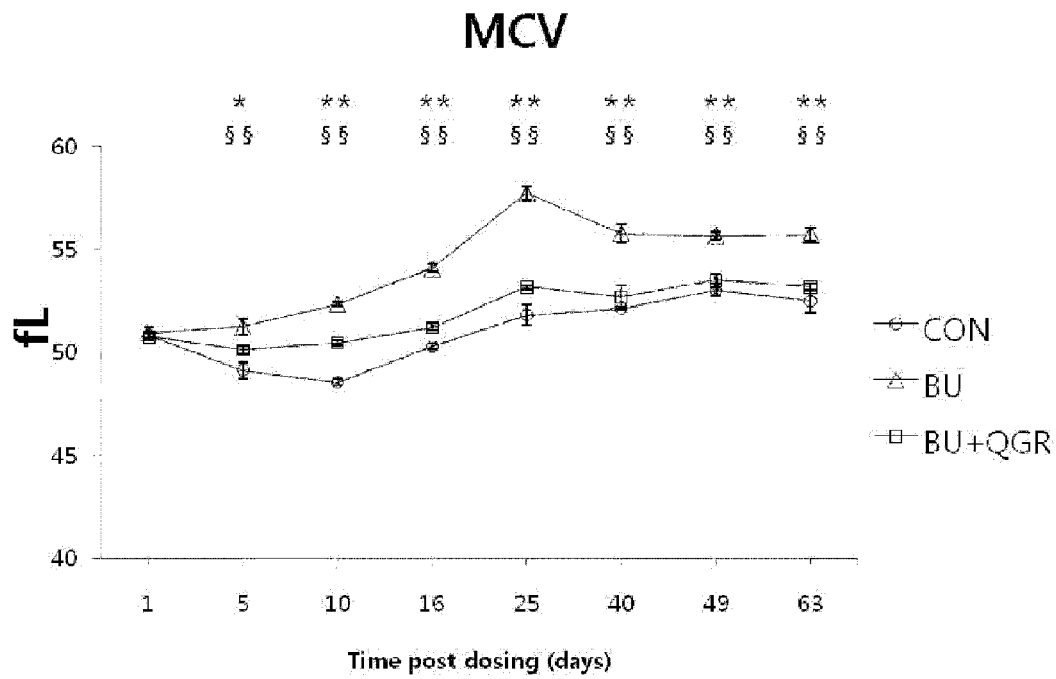
FIG. 9e shows the change of mean corpuscular volume (MCV). In case of anemia, MCV is up-regulated by the compensatory reaction to recover the anemia. According to the data shown in FIG. 9e, the MCV level of BU administration group is significantly lower than that of BU+QGR administration group (**: p<0.01, *: p<0.05).

FIG. 9e shows the change of mean corpuscular volume (MCV). In case of anemia, MCV is up-regulated by the compensatory reaction to recover the anemia. According to the data shown in FIG. 9e, the MCV levels of BU administration group are significantly lower than those of BU+QGR administration group (**: $p<0.01$, *: $p<0.05$).

Figure 9F:
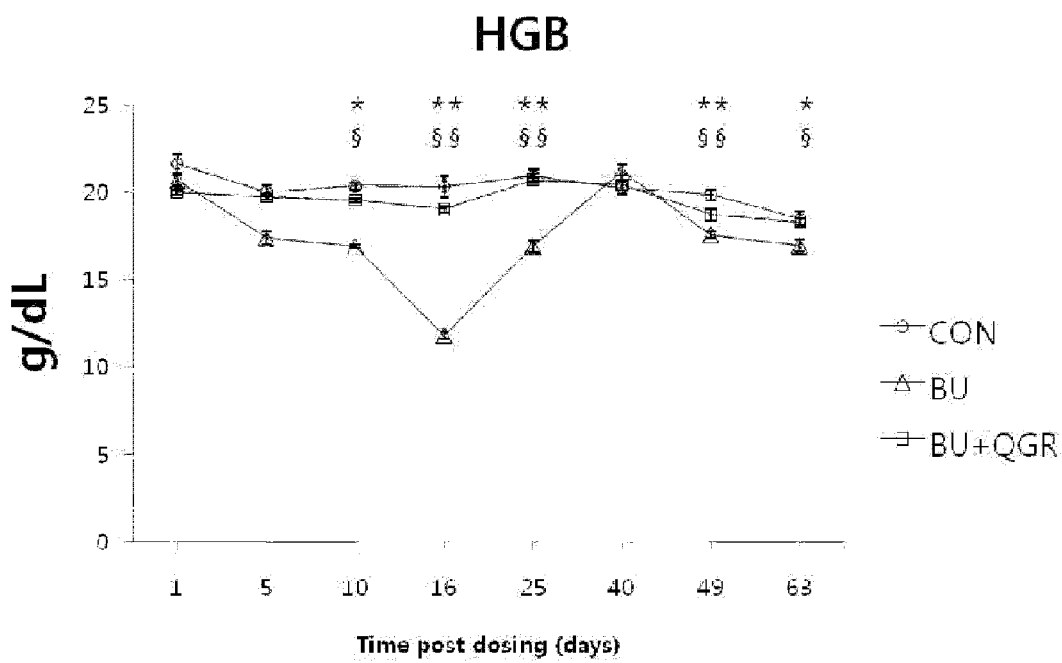
FIG. 9f shows the change of hemoglobin (HGB) level. The pattern of HGB level change is similar to that of erythrocytes in FIG. 9a. That is, QGR recovered the anemia which was induced by the BU administration (**: p<0.01, *: p<0.05).

FIG. 9f shows the change of hemoglobin (HGB) level. The pattern of HGB level change is similar to that of erythrocytes in FIG. 9a. That is, QGR recovered the anemia which was induced by the BU administration.

Figure 9G:
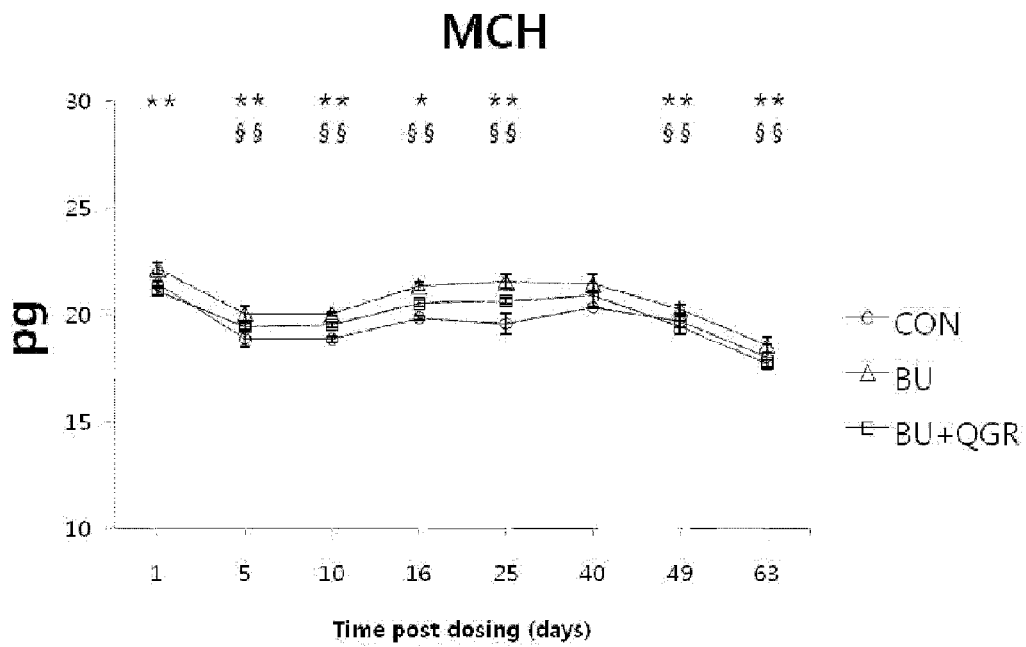
FIG. 9g shows the change of the mean corpuscular hemoglobin (MCH) (**: p<0.01, *: p<0.05).

FIG. 9g shows the change of the mean corpuscular hemoglobin (MCH).

(2) Flow Cytometry Analysis of Bone Marrow Cells

Figure 10A:
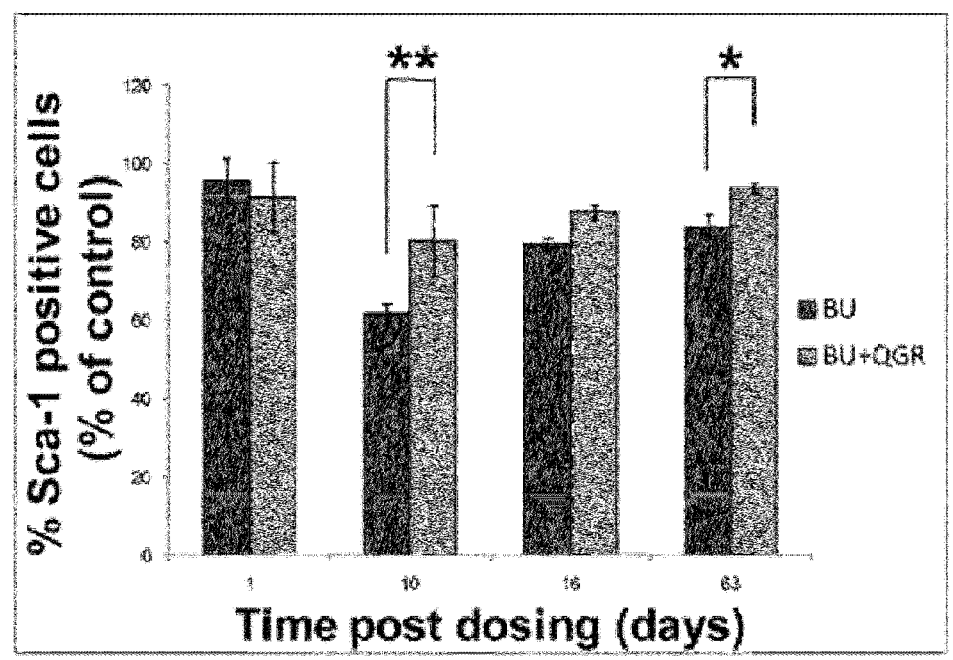
FIG. 10a shows the number of cells positive for Sca-1 measured time dependently by flow cytometry in the positive control group and experimental group respectively. The Sca-1 expresses in hematopoietic stem/progenitor cells (HSPCs). The numbers of cells positive for Sca-1 increased in the experimental group after 10 days of QGR administration (**: p<0.01, *: p<0.05).

FIG. 10a shows the number of cells positive for Sca-1 measured time dependently by flow cytometry in the positive control group and experimental group respectively. The Sca-1 expresses in hematopoietic stem/progenitor cells (HSPCs). The numbers of cells positive for Sca-1 increased in the experimental group after 10 days of QGR administration (**: $p<0.01$, *: $p<0.05$).

Figure 10B:
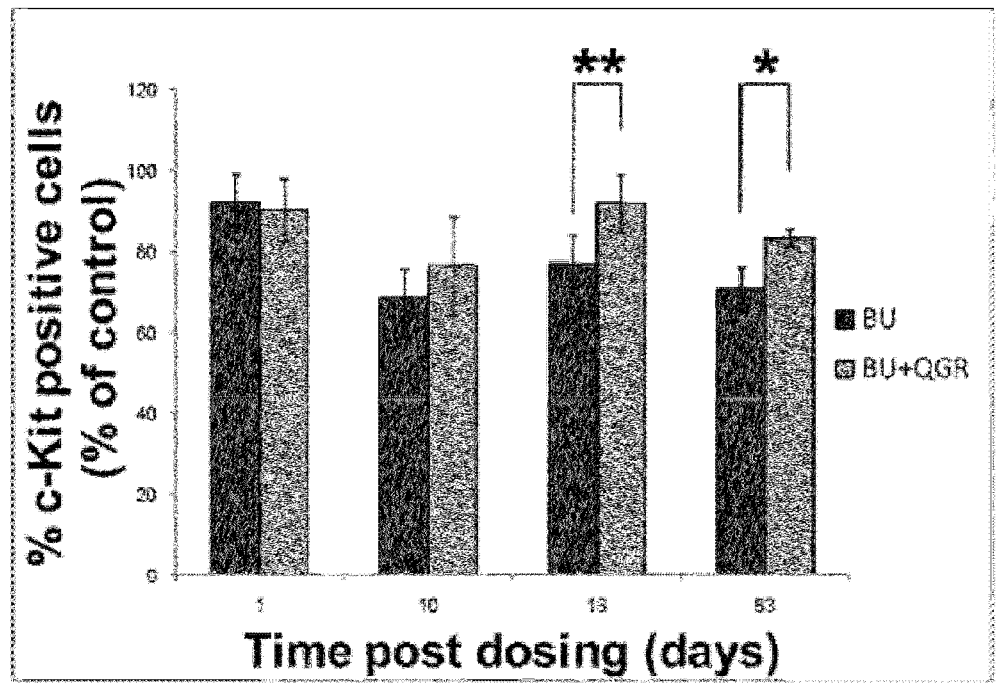
FIG. 10b shows the number of cells positive for c-kit measured time dependently by flow cytometry in the positive control group and experimental group respectively. The c-kit is other marker expressed in HSPCs. The number of cells positive for c-kit increased in the experimental group after 10 days of QGR administration and the significant difference (**: p<0.01, *: p<0.05) from the positive control group appeared at 16 days after QGR administration.

FIG. 10b shows the c-kit positive cell numbers measured time dependently by flow cytometry in the positive control group and experimental group respectively. The c-kit is another marker expressed in hematopoietic stem/progenitor cells (HSPCs). The number of c-kit positive cells increased in the experimental group at 10 days after QGR administration and the significant difference (**: $p<0.01$, *: $p<0.05$) from the positive control group appeared at 16 days after QGR administration.

Figure 10C:
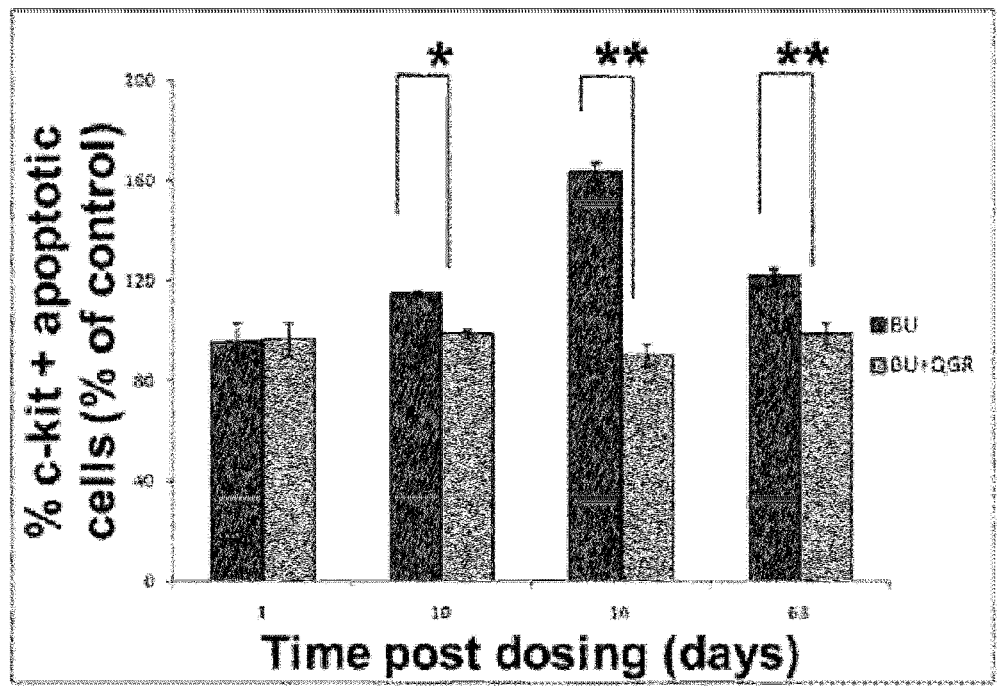
FIG. 10c shows the number of apoptotic HSPCs measured time dependently in the positive control group and experimental group respectively and comparison between the groups. The number of dead HSPCs significantly increased from 10 days of QGR administration in the positive control group. However there was no change in the experimental group (**: p<0.01, *: p<0.05).

FIG. 10c shows the number of apoptotic HSPCs measured time dependently in the positive control group and experimental group respectively and comparison between the groups. The number of dead HSPCs significantly increased from 10 days of QGR administration in the positive control group. However there was no change in the experimental group (**: $p<0.01$, *: $p<0.05$).

Figure 10D:
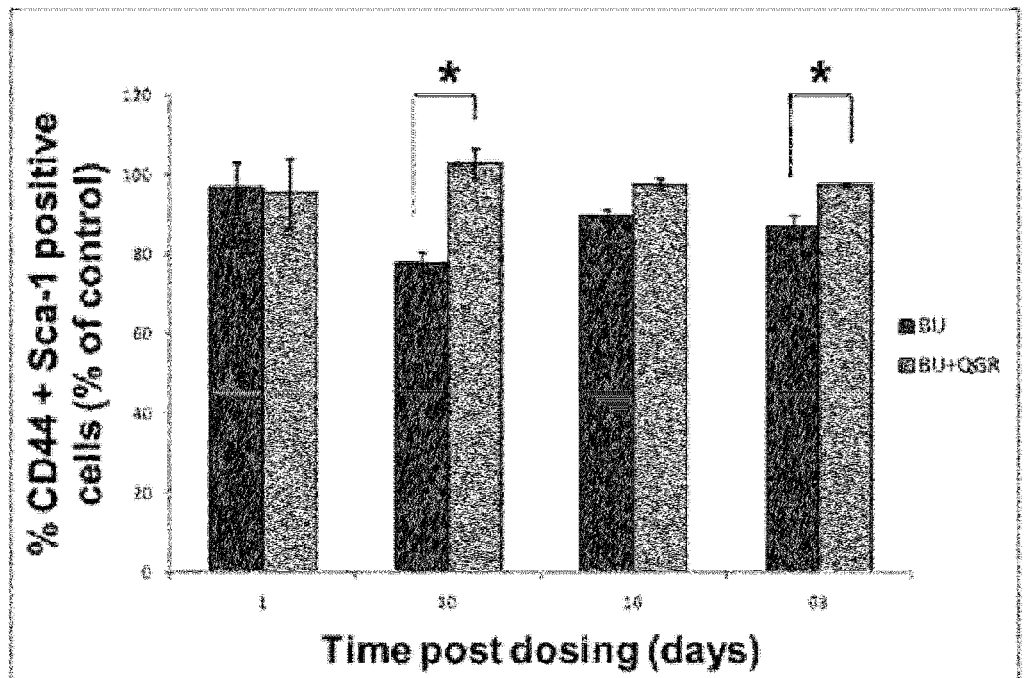
FIG. 10d shows the number of mesenchymal stem/progenitor cells (MSPCs) measured time dependently in the positive control group and the experimental group respectively and comparison between the groups. The number of CD44$^+$Sca-1$^+$ cells simultaneously expressing CD44 and Sca-1 which are specific markers for MSPCs remarkably decreased in the positive control group. However, there was no change in the experimental group. These experimental data indicates that mesenchymal stem cells damaged by BU administration were recovered by QGR.

FIG. 10d shows the number of mesenchymal stem/progenitor cells (MSPCs) measured time dependently in the positive control group and the experimental group. The number of $CD44^+Sca-1^+$ cells expressing simultaneously CD44 and Sca-1 which are specific markers for MSPCs remarkably decreased in the positive control group. However, there was no change in the experimental group. These experimental data indicates that mesenchymal stem cells damaged by BU administration were recovered by QGR.

(3) Semisolid Colonogenic Assay for Measuring BFU-E

Figure 11:
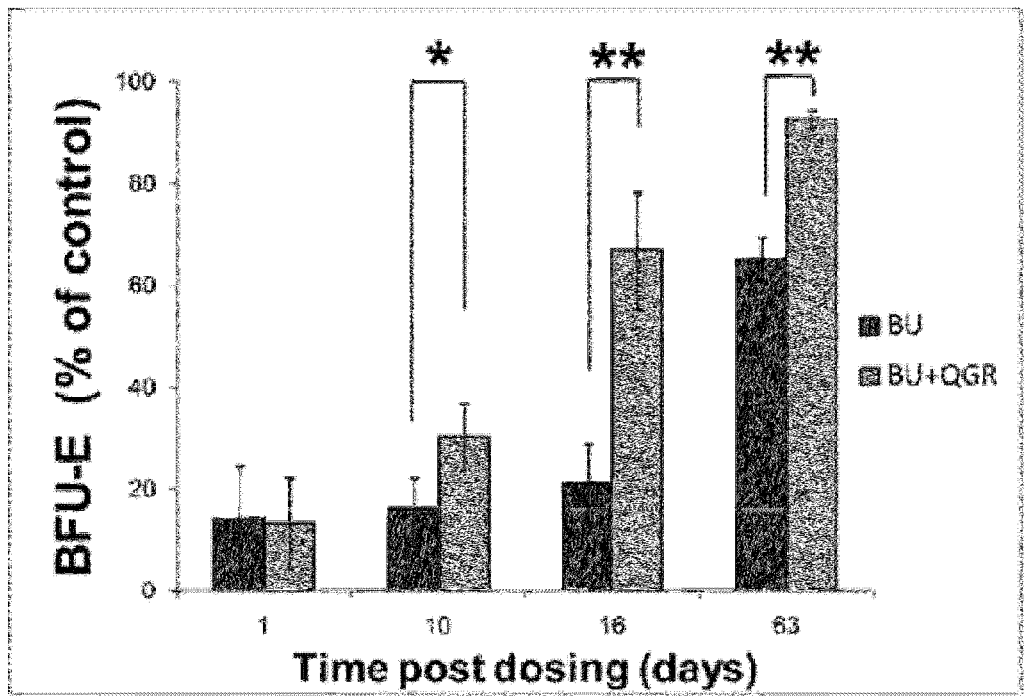
FIG. 11 shows the number of specific progenitor BFU-E measured time dependently in the positive control group and the experimental group respectively. BFU-E is formed during the differentiation from hematopoietic stem cells to erythrocyte. In the experimental group, the number of BFU-E increased significantly and consistently from 10 days to 63 days after QGR administration (**: p<0.01, *: p<0.05). These experimental data indicates that QGR can actively stimulate erythropoiesis in the differentiation process from hematopoietic stem cells to erythrocyte.

FIG. 11 shows the number of BFU-E measured time dependently in the positive control group and the experimental group respectively. BFU-E, a specific progenitor colony of erythrocytes, is formed early during the differentiation from hematopoietic stem cells to erythrocytes. In the experimental group, the number of BFU-E increased significantly and consistently from 10 days to 63 days after QGR administration (**: $p<0.01$, *: $p<0.05$). These experimental data indicates that QGR can actively stimulate erythropoiesis in the differentiation from hematopoietic stem cells to erythrocyte.

(4) Isolation of Mesenchymal Stem Cells and Measurement of Colony-Forming Unit-Fibroblast (CFU-F)

Figure 12:
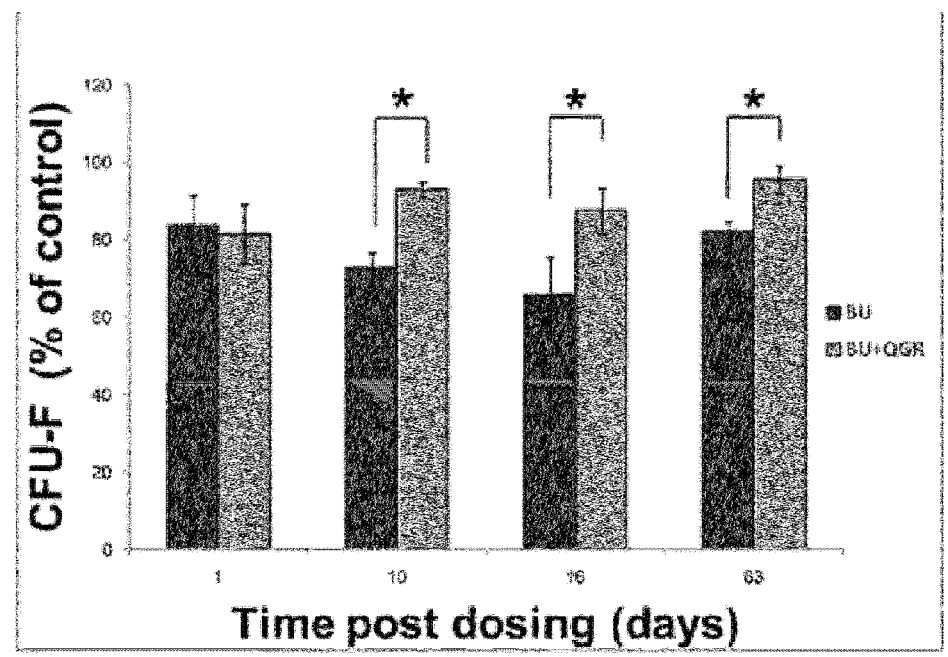
FIG. 12 shows the number of CFU-F measured time dependently in the positive control group and experimental group. CFU-F is formed through the differentiation process from mesenchymal stem cells. In the positive control group, the number of CFU-F decreased from day 10. However, the CFU-F number recovered significantly in the experimental group (*: p<0.05). These data indicates that QGR can affect positively the formation of cells which function as hematopoietic stem cell niche. Accordingly, it is demonstrated that QGR can stimulate hematopoiesis through the action of recovering stem cell niche which was damaged by BU administration.

FIG. 12 shows the number of CFU-F measured time dependently in the positive control group and experimental group. CFU-F is a progenitor colony differentiated from mesenchymal stem cells. In the positive control group, the number of CFU-F decreased from day 10. However, the number recovered significantly in the experimental group (*: $p<0.05$). These data indicates that QGR can affect positively the formation of cells which function as hematopoietic stem cells niche. Accordingly, it is demonstrated that QGR can stimulate hematopoiesis through the action of recovering stem cell niche which was damaged by BU administration.

Figure 13A:
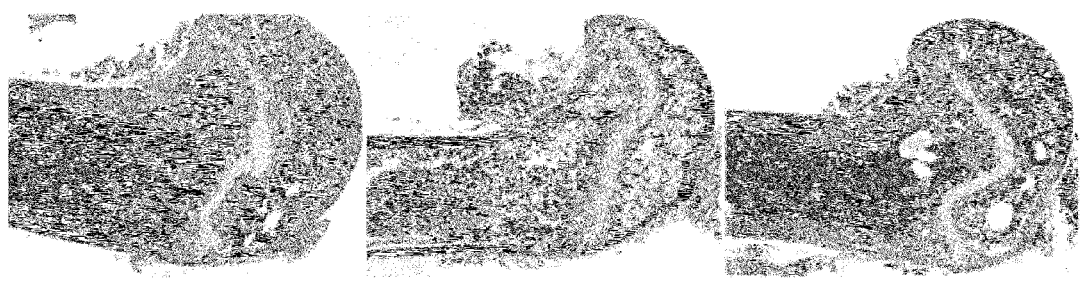
FIG. 13a represents histopathological features of bone marrow of humerus. The number of cells in bone marrow remarkably decreased in the positive control group (middle) compared to that of normal control group (left). However, the number of cells in bone marrow has been recovered in the experimental group (right).

(5) Histopathological Features of Bone Marrow and Measurement of Osteoid Formation FIG. 13a represents histopathological features of bone marrow of humerus. The cellularity of bone marrow remarkably decreased in the positive control group (middle) compared to that of normal control group (left). However, the number of cells in bone marrow has been recovered in the experimental group (right).

Figure 13B:
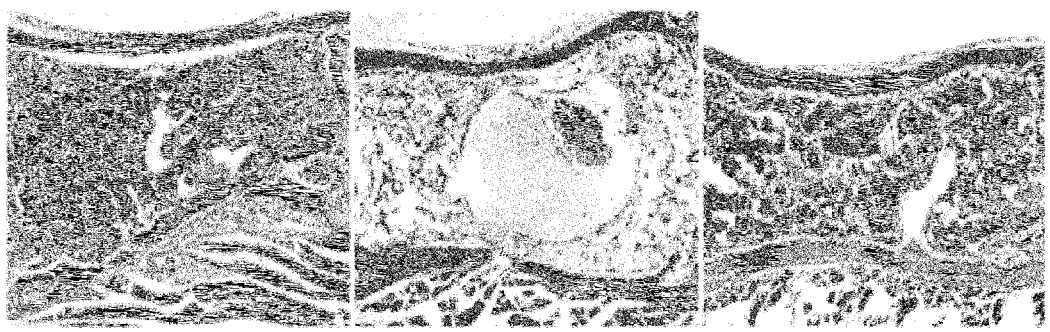
FIG. 13b represents a damaged feature of sinusoid endothelium in bone marrow. The number of bone marrow cells was in the normal range and no sinusoid damage was observed in the normal control group (left). However, severely damaged sinusoids were observed in the positive control group (middle). The damaged sinusoids were recovered in the experimental group (right).

FIG. 13b shows representatives of sinusoidal endothelia in the bone marrow. The normal endothelia in the normal control group (left), severely damaged sinusoids in the positive control group (middle) and recovered sinosoids in the experimental group (right) are represented.

Figure 13C:
FIG. 13c shows the degree of osteoid formation. Goldner's trichrome stain for osteoid was carried out. Redly stained osteoid was actively formed in the experimental group (right) compared to the positive control group (middle).

FIG. 13c shows the degree of osteoid formation. Goldner's trichrome staining for osteoid was carried out. Redly stained osteoid is actively formed in the experimental group (right) compared to the positive control group (middle).

Figure 13D:
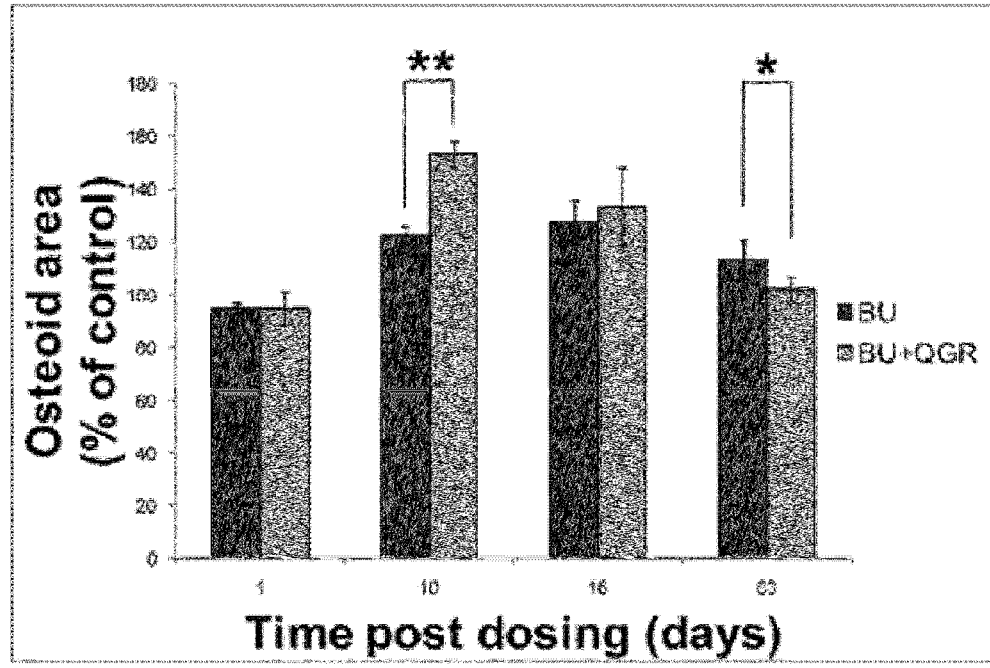
FIG. 13d shows quantification of osteoid formation in FIG. 13c. The area of osteoid formation increased significantly from day 10 of QGR administration in the experimental group compared to that of the positive control group (**: p<0.01, *: p<0.05).

FIG. 13d shows the quantification of osteoid formation in FIG. 13c. The area of osteoid formation increased significantly from day 10 after QGR administration in the experimental group compared to that of the positive control group (**: $p<0.01$, *: $p<0.05$).

Figure 13E:
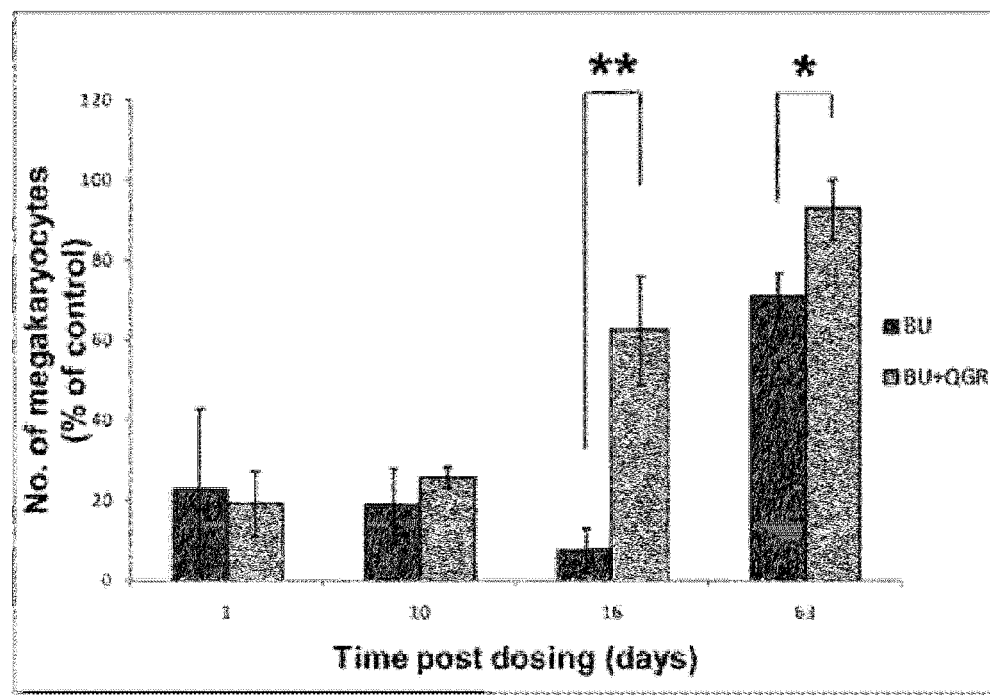
FIG. 13e shows the number of megakaryocytes surrounding sinusoids measured time dependently and comparisons between the groups. The number of megakaryocytes increased from day 16 of QGR administration in the experimental group compared to that of the positive control group (**: p<0.01, *: p<0.05).

FIG. 13e shows the number of megakaryocytes surrounding sinusoid measured time dependently and comparisons between the groups. The number of megakaryocytes increased from day 16 after QGR administration in the experimental group compared to that of the positive control group (**: $p<0.01$, *: $p<0.05$).

Figure 13F:
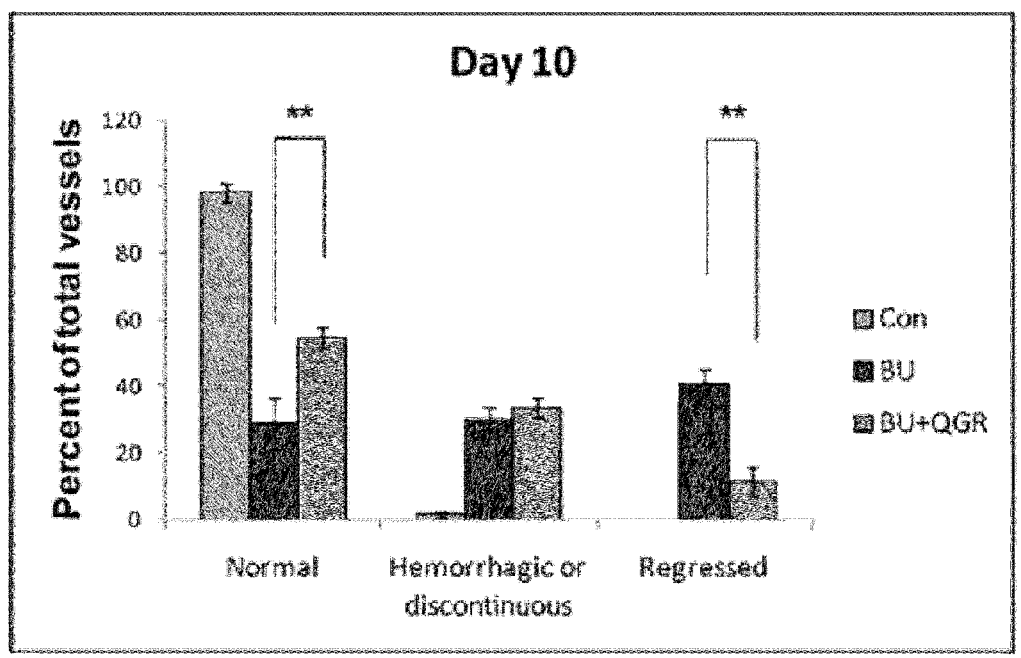
FIG. 13f shows the comparison of the sinusoidal damage among the respective groups at day 10. The morphology of sinusoid damage was measured and classified as normal, hemorrhagic or discontinuous, and regressed. The number of normal sinusoid in the experimental group (BU+QGR) was greater than that of the positive control group (BU). Furthermore, the number of regressed sinusoid was significantly decreased in the experimental group (**: p<0.01, *: p<0.05).

FIG. 13f shows the comparison of the sinusoidal damage among the respective groups at day 10. The morphology of sinusoid damage was measured and classified as normal, hemorrhagic or discontinuous, and regressed. The number of normal sinusoid in the experimental group (BU+QGR) was greater than that of the positive control group (BU). Furthermore, the number of regressed sinusoid was significantly decreased in the experimental group (**: $p<0.01$, *: $p<0.05$).

Figure 13G:
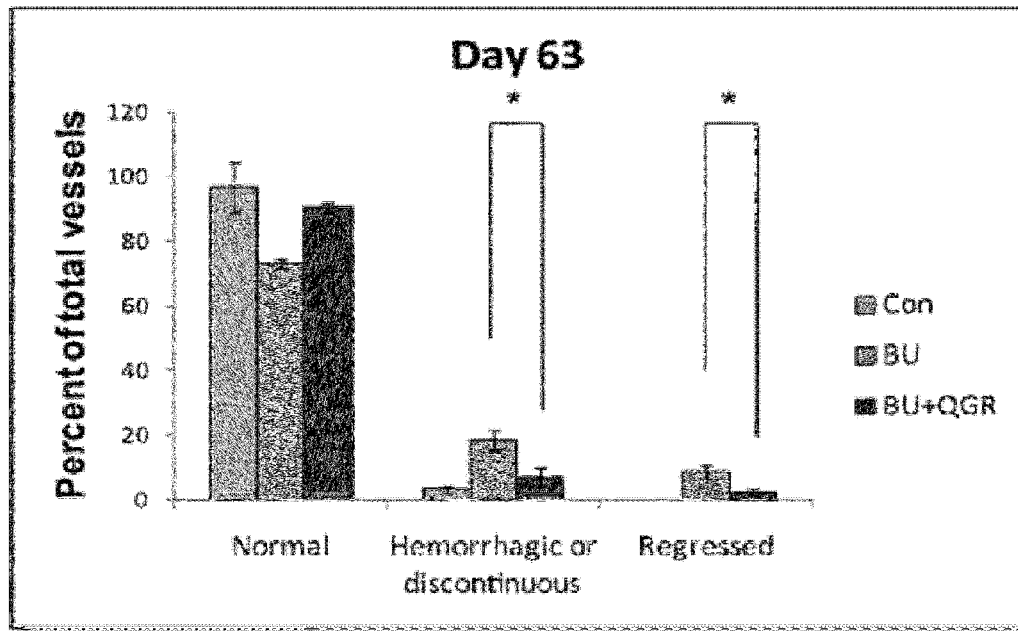
FIG. 13g shows the comparison of the sinusoidal damage among the respective groups at day 63. The number of normal sinusoids increased in BU+QGR group. Moreover, the numbers of hemorrhagic sinusoids and regressed sinusoids significantly decreased by QGR treatment (**: p<0.01, *: p<0.05).

FIG. 13g shows the comparison of the sinusoidal damage among the respective groups at day 63. The number of normal sinusoids increased in BU+QGR group. Moreover, the numbers of hemorrhagic sinusoids and regressed sinusoids significantly decreased by QGR treatment (**: $p<0.01$, *: $p<0.05$).

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method of promoting hematopoiesis comprising administering an effective amount of quercetin 3-O-β-(2"-galloyl)-rhamnopyranoside represented by the following formula 1 to a subject in need of promoting of hematopoiesis

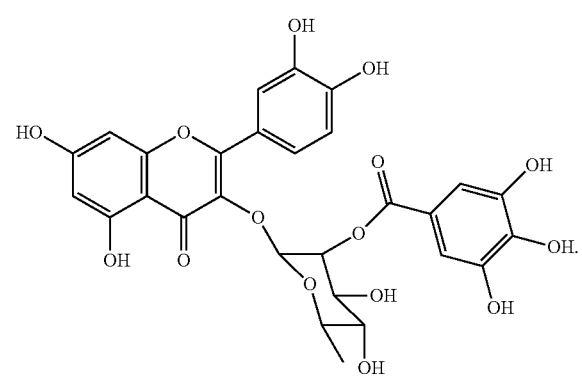

2. The method according to claim 1, wherein the promoting of hematopoiesis is a process of promoting hematopoiesis from hematopoietic stem cells.

3. The method according to claim 2, wherein the hematopoiesis is erythropoiesis, leukopoiesis, or thrombopoiesis.

4. A method of treating or alleviating cytopenia comprising administering an effective amount of quercetin 3-O-β-(2"-galloyl)-rhamnopyranoside represented by the following formula 1 to a subject suffering from cytopenia

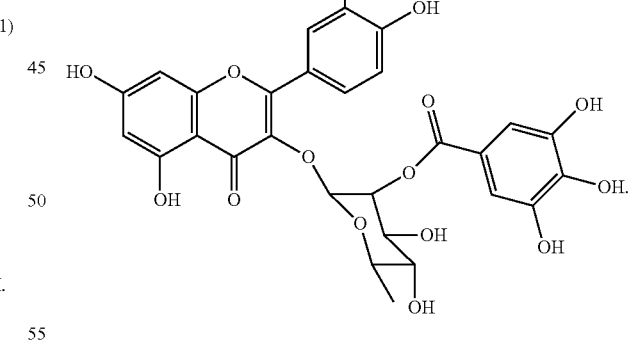

5. The method according to claim 4, wherein the cytopenia is erythropenia, leukopenia, granulocytopenia, neutropenia, thrombocytopenia, pancytopenia, anemia, aplastic anemia, myelodysplasia, or chemotherapy-induced cytopenia.

6. A method of treating or alleviating bone marrow failure comprising administering an effective amount of quercetin 3-O-β-(2"-galloyl)-rhamnopyranoside represented by the following formula 1 to a subject suffering from bone marrow failure

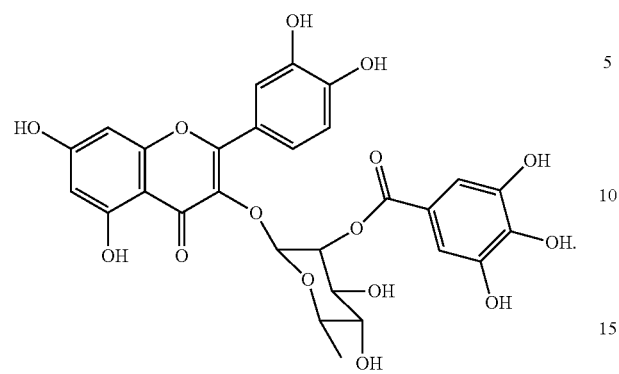
(1)
7. The method according to claim 6, wherein the quercetin 3-O-β-(2"-galloyl)-rhamnopyranoside stimulates a megakaryocyte formation surrounding the blood system of damaged bone marrow, an osteoid formation, or a bone marrow restoration through a recovery of damaged bone marrow microenvironment.
* * * * *

SEQUENCE LISTING

<160> NUMBER OF SEQ ID NOS: 4

<210> SEQ ID NO 1
<211> LENGTH: 26
<212> TYPE: DNA
<213> ORGANISM: Artificial Sequence
<220> FEATURE:
<223> OTHER INFORMATION: RT-PCR primer

<400> SEQUENCE: 1

```
tgcatcctgc accaccaact gcttag                                26

<210> SEQ ID NO 2
<211> LENGTH: 25
<212> TYPE: DNA
<213> ORGANISM: Artificial Sequence
<220> FEATURE:
<223> OTHER INFORMATION: RT-PCR primer

<400> SEQUENCE: 2
cattacaaaa ctggtggcaa atctt                                 25

<210> SEQ ID NO 3
<211> LENGTH: 25
<212> TYPE: DNA
<213> ORGANISM: Artificial Sequence
<220> FEATURE:
<223> OTHER INFORMATION: RT-PCR primer

<400> SEQUENCE: 3 gcccccaac tccggaaacg gactg                                  25

<210> SEQ ID NO 4
<211> LENGTH: 25
<212> TYPE: DNA
<213> ORGANISM: Artificial Sequence
<220> FEATURE:
<223> OTHER INFORMATION: RT-PCR primer

<400> SEQUENCE: 4
agaaaatgtc acgatgggtt gtgca                                 25
```